Figure 1A:
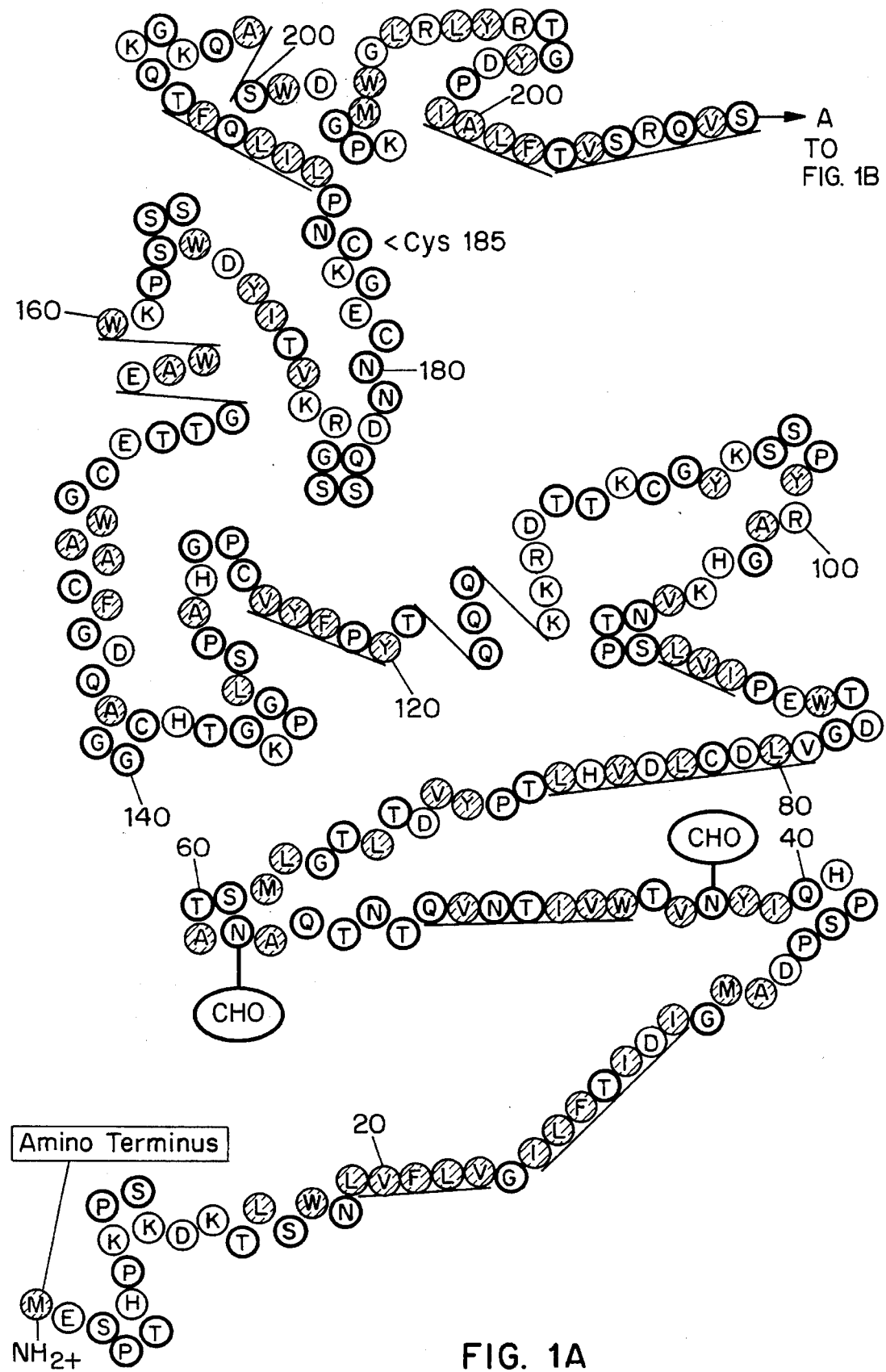

United States Patent [19]

Montelaro et al.

[11] Patent Number: 5,609,876
[45] Date of Patent: Mar. 11, 1997

[54] PEPTIDE VACCINES AND ASSOCIATED METHODS FOR PROTECTION AGAINST FELINE LEUKEMIA VIRUS

[75] Inventors: Ronald C. Montelaro, Wexford, Pa.; J. Darrell Fontenot, Espanola, N.M.

[73] Assignee: University of Pittsburgh of the Commonwealth System of Higher Education, Pittsburgh, Pa.

[21] Appl. No.: 447,925

[22] Filed: May 23, 1995

Related U.S. Application Data

[63] Continuation of Ser. No. 287,474, Aug. 8, 1994, abandoned, which is a continuation of Ser. No. 104,527, Aug. 9, 1993, abandoned.

[51] Int. Cl.$^6$ ................................................ A61K 39/21
[52] U.S. Cl. ..................................... 424/207.1; 530/324
[58] Field of Search ............................. 424/207.1, 187.1; 530/324

[56] References Cited

U.S. PATENT DOCUMENTS 4,789,702  12/1988  Nunberg ................................. 530/324

OTHER PUBLICATIONS

Nick, et al., 1990, Virus Neutralizing and Enhancing Epitodes Characterized by Synthetic Oligo–Peptides Durived from the Feline Leukemia Virus Glycoprotein Sequence, J. Gen. Virol. 71: 77–83.
Pedersen, et al., 1979, Safety and Efficacy Studies of Live–and Killed–Feline Leukemia Virus Vaccines, Am, J. Vet. Res. 40: 1120–1126.
Hoover, et al., 1991, Protection Against Feline Leukemia Virus Infection By Use of Innactivated Virus Vaccine, J. Am. Vet. Med. Assoc. 199: 1392–1401.
Nicolaisen–Strouss, 1987, Natural Feline Leukemia Virus Variant Escapes Neutralization By a Monoclonal Antibody via Amino Acid Change Outside the Antibody–Binding Epitope, J. of Virol. 61: 3410–3415.
Pedersen, et al., 1986, Possible Amino Enhancement Immunoenhancement of Persistent Viremia by Feline Leukemia Virus Envelope Glycoprotein Vaccines in a Challenge–Exposure Situations Where Whole Innactivated Virus Vaccines Where Protective, Vet. Immunol. Immunopathol. 11: 123–148.
Gilbert, et al., 1987 Feline Leukemia Virus Envelope Protein Expression Encoded by a Recombinant Vaccinia Virus: Apparent Lack of Immunogenicity in Vaccinated Animals, Virus Res. 7: 49–67.
Lewis, et al., L., 1981, Protection Against Feline Leukemia by Vaccination with a Subunit Vaccine, Infect. Immun. 34: 888–894.

Mastro et al., 1986, Feline Leukemia Vaccine: Efficacy, Contents and Probable Mechanism, Vet. Immunol. Immunopath. 11: 205–213.
Lewis, et al., 1988, Feline Leukemia Virus Vaccine: New Developments, Vet. Microbiology 17: 297–308.
Kowalski, et al., 1987, Functional Regions of the Envelope Glycoprotein of Human Immunodeficiency Type 1, Science 237: 1351–1355.
Dalgleish, et al., 1984, The CD (T4) Antigen is an Essential Component of the Receptor for the Aids Retrovirus, Nature 312: 763–766.
Bosch, et al., 1989, Identification of the Fusion Peptide of Primate Immunodeficiency Virus, Science 244:694–697.
Battini, et a l., 1992, Receptor Choice Determinants in the Envelope Glycoproteins of Amphotropic, Xenotropic, and Polytropic Murine Leukemia Viruses, J. Virol. 66: 1468–1475.
Donahue, et al., 1991, Viral Genetic Determinants of T–Cell Killing and Immunodeficiency Disease Induction by the Feline Leukemia Virus FeLV–FAIDS, J. Virol. 65: 4461–4469.
Willey, et al., 1989, Functional Interaction of Constant and Variable Domains of Human Immunodeficiency Virus Type 1 gp120, J. Virol. 63: 3595–3600.
Palker, et al., 1988, Type–Specific Neutralization of the Human Immunodeficiency Virus with Antibodies to Env–Encoded Synthetic Peptides, Proc.Natl. Acad. Sci. USA 85: 1932–1936
Dyson, et al., 1992, Immunogenic Peptides Corresponding to the Dominant Antigenic Region Alanine–597 to Cysteine–619 in the Transmembrane Protein of Simian Immunodeficiency Virus Have a Propensity to Fold in Aqueous Solution, Biochemistry 31: 1458–1463.
Nunberg, et al., 1984, Method to Map Antigenic Determinants Recognized by Monoclonal Antibodies: Localization of a Determinant Virus Neutralization on the Feline Leukemia Virus Envelope Protein GP70, Proc. Natl. Acad. Sci. USA 81: 3675–3679.
Elder et al (1987). J. Virol. 61(1), 8–15.
Weijer et al. (1993) Vaccine 11(9), 946–956.

*Primary Examiner*—David Guzo
*Assistant Examiner*—John S. Brusca
*Attorney, Agent, or Firm*—Brumbaugh, Graves, Donohue & Raymond

[57] ABSTRACT

The present invention discloses peptide vaccines and associated methods for protection against feline leukemia virus (FeLV). The synthetic peptides of the present invention retain their secondary structural identity, stimulate antibodies reactive to the whole virus and elicit a cellular response in vaccinations. These synthetic peptides are inexpensive to produce, stable and permit easy differentiation of vaccinated versus FeLV-infected cats.

12 Claims, 6 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
       ( A ) LENGTH: 60 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
       ( A ) ORGANISM: Feline leukemia virus
       ( B ) STRAIN: 61E ( x i ) SEQUENCE DESCRIPTION: SEQ ID NO:1:

```
Thr  Ile  Thr  Pro  Pro  Gln  Ala  Met  Gly  Pro  Asn  Leu  Val  Leu  Pro  Asp
1                  5                        10                       15

Gln  Lys  Pro  Pro  Ser  Arg  Gln  Ser  Gln  Thr  Gly  Ser  Lys  Val  Ala  Thr
                  20                       25                       30

Gln  Arg  Pro  Gln  Thr  Asn  Glu  Ser  Ala  Pro  Arg  Ser  Val  Ala  Pro  Thr
             35                       40                  45

Thr  Val  Gly  Pro  Lys  Arg  Ile  Gly  Thr  Gly  Asp  Arg
        50                       55                  60
```

( 2 ) INFORMATION FOR SEQ ID NO:2:

( i ) SEQUENCE CHARACTERISTICS:
       ( A ) LENGTH: 42 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
       ( A ) ORGANISM: Feline leukemia virus
       ( B ) STRAIN: 61E ( x i ) SEQUENCE DESCRIPTION: SEQ ID NO:2:

```
Thr  Pro  Pro  Gln  Ala  Met  Gly  Pro  Asn  Leu  Val  Leu  Pro  Asp  Gln  Lys
1                  5                        10                       15

Pro  Pro  Ser  Arg  Gln  Ser  Gln  Thr  Gly  Ser  Lys  Val  Ala  Thr  Gln  Arg
             20                       25                       30

Pro  Gln  Thr  Asn  Glu  Ser  Ala  Pro  Arg  Ser
             35                  40
```

( 2 ) INFORMATION FOR SEQ ID NO:3:

( i ) SEQUENCE CHARACTERISTICS:
       ( A ) LENGTH: 21 amino acids
       ( B ) TYPE: amino acid ( C ) STRANDEDNESS: single
           ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
           ( A ) ORGANISM: Feline leukemia virus
           ( B ) STRAIN: 61E ( x i ) SEQUENCE DESCRIPTION: SEQ ID NO:3:

Thr  Pro  Pro  Gln  Ala  Met  Gly  Pro  Asn  Leu  Val  Leu  Pro  Asp  Gln  Lys
    1                   5                        10                       15

Pro  Pro  Ser  Arg  Gln
                    20

( 2 ) INFORMATION FOR SEQ ID NO:4:

( i ) SEQUENCE CHARACTERISTICS:
           ( A ) LENGTH: 21 amino acids
           ( B ) TYPE: amino acid
           ( C ) STRANDEDNESS: single
           ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
           ( A ) ORGANISM: Feline leukemia virus
           ( B ) STRAIN: 61E ( x i ) SEQUENCE DESCRIPTION: SEQ ID NO:4:

Ser  Gln  Thr  Gly  Ser  Lys  Val  Ala  Thr  Gln  Arg  Pro  Gln  Thr  Asn  Glu
    1                   5                        10                       15

Ser  Ala  Pro  Arg  Ser
                    20

( 2 ) INFORMATION FOR SEQ ID NO:5:

( i ) SEQUENCE CHARACTERISTICS:
           ( A ) LENGTH: 16 amino acids
           ( B ) TYPE: amino acid
           ( C ) STRANDEDNESS: single
           ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
           ( A ) ORGANISM: Feline leukemia virus
           ( B ) STRAIN: 61E ( x i ) SEQUENCE DESCRIPTION: SEQ ID NO:5:

Val  Ala  Pro  Thr  Thr  Val  Gly  Pro  Lys  Arg  Ile  Gly  Thr  Gly  Asp  Arg
    1                   5                        10                       15

( 2 ) INFORMATION FOR SEQ ID NO:6:

( i ) SEQUENCE CHARACTERISTICS:
    ( A ) LENGTH: 445 amino acids
    ( B ) TYPE: amino acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Feline leukemia virus
    ( B ) STRAIN: 61E ( x i ) SEQUENCE DESCRIPTION: SEQ ID NO:6:

| Met | Glu | Ser | Pro | Thr | His | Pro | Lys | Pro | Ser | Lys | Asp | Lys | Thr | Leu | Ser |
|---|---|---|---|---|---|---|---|---|---|---|---|---|---|---|---|
| 1 | | | | 5 | | | | | 10 | | | | | 15 | |
| Trp | Asn | Leu | Val | Phe | Leu | Val | Gly | Ile | Leu | Phe | Thr | Ile | Asp | Ile | Gly |
| | | | 20 | | | | 25 | | | | | 30 | | | |
| Met | Ala | Asp | Pro | Ser | Pro | His | Gln | Ile | Tyr | Asn | Val | Thr | Trp | Val | Ile |
| | | 35 | | | | 40 | | | | | 45 | | | | |
| Thr | Asn | Val | Gln | Thr | Asn | Thr | Gln | Ala | Asn | Ala | Thr | Ser | Met | Leu | Gly |
| | 50 | | | | | 55 | | | | | 60 | | | | |
| Thr | Leu | Thr | Asp | Val | Tyr | Pro | Thr | Leu | His | Val | Asp | Leu | Cys | Asp | Leu |
| 65 | | | | | 70 | | | | 75 | | | | | | 80 |
| Val | Gly | Asp | Thr | Trp | Glu | Pro | Ile | Val | Leu | Ser | Pro | Thr | Asn | Val | Lys |
| | | | | 85 | | | | | 90 | | | | | 95 | |
| His | Gly | Ala | Arg | Tyr | Pro | Ser | Ser | Lys | Tyr | Gly | Cys | Lys | Thr | Thr | Asp |
| | | | 100 | | | | | 105 | | | | | 110 | | |
| Arg | Lys | Lys | Gln | Gln | Gln | Thr | Tyr | Pro | Phe | Tyr | Val | Cys | Pro | Gly | His |
| | | 115 | | | | | 120 | | | | | 125 | | | |
| Ala | Pro | Ser | Leu | Gly | Pro | Lys | Gly | Thr | His | Cys | Gly | Gly | Ala | Gln | Asp |
| | 130 | | | | | 135 | | | | | 140 | | | | |
| Gly | Phe | Cys | Ala | Ala | Trp | Gly | Cys | Glu | Thr | Thr | Gly | Glu | Ala | Trp | Trp |
| 145 | | | | | 150 | | | | | 155 | | | | | 160 |
| Lys | Pro | Ser | Ser | Ser | Trp | Asp | Tyr | Ile | Thr | Val | Lys | Arg | Gly | Ser | Ser |
| | | | | 165 | | | | | 170 | | | | | 175 | |
| Gln | Asp | Asn | Asn | Cys | Glu | Gly | Lys | Cys | Asn | Pro | Leu | Ile | Leu | Gln | Phe |
| | | | 180 | | | | | 185 | | | | | 190 | | |
| Thr | Gln | Lys | Gly | Lys | Gln | Ala | Ser | Trp | Asp | Gly | Pro | Lys | Met | Trp | Gly |
| | | 195 | | | | | 200 | | | | | 205 | | | |
| Leu | Arg | Leu | Tyr | Arg | Thr | Gly | Tyr | Asp | Pro | Ile | Ala | Leu | Phe | Thr | Val |
| | 210 | | | | | 215 | | | | | 220 | | | | |
| Ser | Arg | Gln | Val | Ser | Thr | Ile | Thr | Pro | Pro | Gln | Ala | Met | Gly | Pro | Asn |
| 225 | | | | | 230 | | | | | 235 | | | | | 240 |
| Leu | Val | Leu | Pro | Asp | Gln | Lys | Pro | Pro | Ser | Arg | Gln | Ser | Gln | Thr | Gly |
| | | | 245 | | | | | 250 | | | | | 255 | | |
| Ser | Lys | Val | Ala | Thr | Gln | Arg | Pro | Gln | Thr | Asn | Glu | Ser | Ala | Pro | Arg |
| | | | 260 | | | | | 265 | | | | | 270 | | |
| Ser | Val | Ala | Pro | Thr | Thr | Val | Gly | Pro | Lys | Arg | Ile | Gly | Thr | Gly | Asp |
| | | 275 | | | | | 280 | | | | | 285 | | | |
| Arg | Leu | Ile | Asn | Leu | Val | Gln | Gly | Thr | Tyr | Leu | Ala | Leu | Asn | Ala | Thr |
| | 290 | | | | | 295 | | | | | 300 | | | | |
| Asp | Pro | Asn | Lys | Thr | Lys | Asp | Cys | Trp | Leu | Cys | Leu | Val | Ser | Arg | Pro |
| 305 | | | | 310 | | | | | 315 | | | | | | 320 |
| Pro | Tyr | Tyr | Glu | Gly | Ile | Ala | Ile | Leu | Gly | Asn | Tyr | Ser | Asn | Gln | Thr |

|     |     |     | 325 |     |     |     |     | 330 |     |     |     | 335 |     |     |
| --- | --- | --- | --- | --- | --- | --- | --- | --- | --- | --- | --- | --- | --- | --- |
| Asn | Pro | Pro | Pro | Ser | Cys | Leu | Ser | Ile | Pro | Gln | His | Lys | Leu | Thr | Ile |
|     |     |     | 340 |     |     |     |     | 345 |     |     |     | 350 |     |     |
| Ser | Glu | Val | Ser | Gly | Gln | Gly | Leu | Cys | Ile | Gly | Thr | Val | Pro | Lys | Thr |
|     |     | 355 |     |     |     |     | 360 |     |     |     |     | 365 |     |     |
| His | Gln | Ala | Leu | Cys | Asn | Lys | Thr | Gln | Gln | Gly | His | Thr | Gly | Ala | His |
|     | 370 |     |     |     |     | 375 |     |     |     |     | 380 |     |     |     |
| Tyr | Leu | Ala | Ala | Pro | Asn | Gly | Thr | Tyr | Trp | Ala | Cys | Asn | Thr | Gly | Leu |
| 385 |     |     |     |     | 390 |     |     |     |     | 395 |     |     |     |     | 400 |
| Thr | Pro | Cys | Ile | Ser | Met | Ala | Val | Leu | Asn | Trp | Thr | Ser | Asp | Phe | Cys |
|     |     |     |     | 405 |     |     |     |     | 410 |     |     |     |     | 415 |     |
| Val | Leu | Ile | Glu | Leu | Trp | Pro | Arg | Val | Thr | Tyr | His | Gln | Pro | Glu | Tyr |
|     |     |     | 420 |     |     |     |     | 425 |     |     |     |     | 430 |     |     |
| Val | Tyr | Thr | His | Phe | Ala | Lys | Ala | Val | Arg | Phe | Arg | Arg |     |     |     |
|     |     | 435 |     |     |     |     | 440 |     |     |     |     | 445 |     |     |     |

PEPTIDE VACCINES AND ASSOCIATED METHODS FOR PROTECTION AGAINST FELINE LEUKEMIA VIRUS

This is a continuation, of application Ser. No. 08/287,474, filed Aug. 8, 1994, abandoned, which is a continuation, of application Ser. No. 08/104,527, filed Aug. 9, 1993, abandoned.

1. INTRODUCTION

The present invention relates to synthetic peptide molecules and their use as vaccines to impart immunoprophylaxis against feline leukemia virus (FeLV). A limiting factor in utilizing peptides as vaccines, whether derived through peptide synthesis or isolation of purified protein fragments, is a preference that the peptide retain its structural identity in solution in comparison to the corresponding domain of the native protein. Retaining structural identity may induce a faithful humoral and cytotoxic T-lymphocyte (CTL) response as well as stimulating an immunological memory. An especially preferred embodiment of the invention discloses the synthetic peptide, PRN60, and methods of use as a vaccine against FeLV. The PRN60 peptide may be used either as initial prophylactic protection against an FeLV challenge or as a booster to an initial FeLV vaccine. The PRN60 peptide substantially maintains an ordered, native-like secondary structure similar to that predicted for the corresponding region within the immunodominant region of the FeLV protein, gp70. Additionally, PRN60 elicits both humoral and cellular responses in experimental vaccinations. The peptide vaccines of the present invention are inexpensive to produce, stable and less likely than existing FeLV vaccines to produce unwanted side effects. In addition, peptides utilized as vaccines permit easy differentiation of vaccinated versus FeLV-infected cats through simple serological methods.

2. BACKGROUND OF THE INVENTION

Feline leukemia virus, a horizontally transmitted retrovirus, was first discovered among cats living in an urban environment and having frequent social contact (Jarrett, et al., 1964, Nature 202: 566–567). FeLV is believed to have been the first naturally occurring retrovirus in which contagious spreading was documented (Jarrett, et al., 1964, Nature 202: 566–567; Kawakami, et al., 1967, Science 158: 1049–1050). The FeLV retrovirus can cause either proliferative (lymphosarcoma) or antiproliferative diseases (aplastic anemia and immunodeficiency syndrome) in cats (Anderson, et al., 1971, J. Natl. Cancer Inst. 47: 807–817; Hardy, et al., 1976, Cancer Res. 36: 582–588). Regardless of the clinical course of infection, however, the FeLV establishes a permanent infection in the cat that is not eliminated. Therefore, prophylactic vaccines are critical to prevent FeLV infection in cats.

A viral vaccine should be designed such that both a humoral and CTL response is achieved, as well as stimulating a useful immunological memory. Examples of potential vaccines against viral infection include attenuated or inactivated whole virus, purified viral macromolecules (such as envelope proteins or capsular polysaccharides), recombinant antigen vaccines, recombinant vector vaccines and synthetic subunit vaccines.

The most common type of viral vaccine developed to date have been whole organism vaccines that are either attenuated or inactivated. An attenuated viral vaccine is a virus that has lost its pathogenicity, but not its ability for transient growth within the host. Major advantages of the attenuated viral vaccine include prolonged exposure to the immune system due its ability for transient growth as well as its ability to induce both a humoral and CTL response. Since an attenuated viral vaccine is a mutant, avirulent organism selected from culturing of a wild type, virulent organism, the possibility exists that the attenuated viral vaccine could revert to a virulent form subsequent to host vaccination. An inactivated viral vaccine is usually produced by exposing a virulent strain to either chemical or radiation treatment. Such inactivated strains cannot, as a rule, revert to a virulent strain. However, such vaccines tend to induce only a humoral immune response and usually require multiple boosters due to an inability to grow transiently within the host.

Purified macromolecules utilized as a vaccine reduce the risk of reversion to a virulent form. However, utilizing a macromolecule such as an envelope protein or capsular polysaccharide most likely results only in an induction of a humoral response. A CTL response may be induced by proper selection and presentation of an immunizing antigen.

Viral antigen vaccines can be expressed and purified utilizing recombinant DNA techniques. A DNA sequence encoding an antigen determinant is isolated, characterized and subcloned into an appropriate DNA expression vector. The expression vector, (usually plasmid DNA) is transformed into an appropriate host (e.g., *E. coli*, yeast or a mammalian cell line), grown under conditions amenable for expression of the cloned antigen determinant, and purified for use as a vaccine. The recombinant proteins or peptides are usually processed as an exogenous antigen, more often resulting in a humoral but not a CTL response.

A genetically engineered virus can be utilized as a vector. The viral vector contains a recombinant DNA sequence encoding an antigen determinant and is subcloned downstream of a viral vector promoter. The recombinant DNA sequence (again, most likely plasmid DNA) is transferred into the viral vector genome such that the DNA sequence encoding the antigenic determinant is expressed. The recombinant viral vector is then administered, for example, by dermal scratching. A localized infection ensues, allowing the antigen determinant to be expressed, inducing both a humoral and cellular response within the vaccinated host. For a review of these hereinbefore described methods available to the skilled artisan, see Kuby, 1992, In: *Immunology*; Chapter 18, "Vaccines"; W. H. Freeman, New York, N.Y.

Olsen, et al. (1977, Cancer Res., 37: 2082–2085) immunized cats with a combined vaccine composed of a killed FeLV virus and killed feline oncornavirus-associated cell membrane antigen (FOCMA) tumor cells. The combined vaccine did not inhibit the induction of FeLV viremia. (Also, see Pederson, et al., 1979, Am. J. Vet. Res. 40: 1120–1126, which exemplifies the difficulty in generating immunity via vaccination with killed FeLV virus.)

Hoover, et al., (1991, J. Am. Vet. Med. Assoc. 199: 1392–1401) tested inactivated FeLV virus, live FeLV virus and FeLV envelope peptide prototypes as potential vaccines. An inactivated vaccine developed from the FeLV-FAIDS-61E-A isolate protected cats from both homologous and heterologous viral exposure. In contrast, a panel of FeLV-GA-B envelope peptides, including peptides representing portions of the immunodominant domain, major neutralizing domain and variable neutralizing domain of gp70, were unsuccessful in providing resistance against FeLV challenge.

Nicolaisen-Strouss (1987, J. Virol. 61: 3410–3415) identified an FeLV variant that was not neutralized by the 5-amino acid epitope described below by Elder, et al. A single amino acid change (proline to leucine) three amino acids from the NH$_2$-terminus of the 5-amino acid binding epitope was implicated in lowering the affinity for binding the neutralizing antibody.

The FeLV envelope protein, gp70, was substantially purified and used to vaccinate cats (Pederson, et al., 1986, Vet. Immunol. Immunopathol. 11: 123–148). Although serum antibodies were produced, no viral neutralizing antibodies were detected in vaccinated cats. Additionally, gp70 vaccinated cats became more persistently retroviremic than non-immunized cats subsequent to a virulent FeLV challenge.

Gilbert, et al., 1987, Virus Res. 7: 49–67) disclosed a lack of FeLV neutralizing activity or immunoprophylaxis following immunization with a vaccinia vector expressing the env gp85 protein of FeLV-GA-B.

Subunit vaccines to combat FeLV infection were developed utilizing FeLV antigens released from lymphoid cells persistently infected with the Kawakami isolate (Lewis, et al., 1981, Infect. Immun. 34: 888–894; Mastro, et al., 1986, Vet. Immunol. Immonopath. 11: 205–213; reviewed in Lewis, et al., 1988, Vet. Microbiology 17: 297–308). This cell line produces viral coded polypeptides which are subsequently harvested and used to vaccinate cats. These viral antigens compose a non-infectious subunit vaccine which is approximately 80% effective in preventing FeLV viremia.

Subunit vaccines may be designed in attempts to structurally mimic domains of a viral envelope protein, in part due to the fundamental role these proteins play in virus entry into the host cell and subsequent cytopathic effects (Kowalski, et al., 1987, Science 237: 1351–1355). For example, the retrovirus external surface unit (SU) protein is involved in binding to a host cell receptor, followed by a fusion event mediated by the transmembrane (TM) protein (Dalgleish, et al., 1984, Nature 312: 763–766; Bosch, et al., 1989, Science 244: 694–697; Battini, et al., 1992, J. Virol. 66: 1468–1475). Therefore, these proteins may be targeted in immunological strategies for prophylactic or therapeutic treatment of a viral infection.

Absent detailed structural characterization by techniques such as NMR spectroscopy or crystallography, the structure and function of these envelope proteins has been investigated through indirect means. For example, inferences concerning structural and functional domains of retroviral envelope proteins have been investigated by utilizing (1) chimeric viruses (Donahue, et al., 1991, J. Virol. 65: 4461–4469; Battini, et al., 1992, J. Virol. 66: 1468–1475), (2) site-directed mutagenesis (Bosch, et al., 1989, Science 244: 694–697; Willey, 1989, J. Virol. 63: 3595–3600), and (3) small synthetic peptides and specific antibodies (Palker, et al., 1988, Proc. Natl. Acad. Sci. USA 85: 1932–1936; Dyson, et al., 1992, Biochemistry 31: 1458–1463; Nick, et al., 1990, J. Gen. Virol. 71: 77–83).

Nunberg, et al. (1990, Proc. Natl. Acad. Sci. USA 81: 3675–3679) disclosed a method to map antigenic determinants of a specified protein. DNA fragments are generated by DNaseI digestion and subcloned into the β-galactosidase gene of the lambda phage Charon 16. Random peptides representing the coding region of the entire protein are expressed and screened with a specific monoclonal antibody to determine its epitope. Binding of a gp70 neutralizing antibody was mapped to a 14 amino acid region (213–226) of the gp70 protein.

Elder, et al. (1987, J. Virol. 61: 8–15) synthesized short peptides corresponding to regions of FeLV envelope proteins, gp70 and p15E. These peptides were conjugated to keyhole limpit hemocyanin and injected into rabbits to induce anti-peptide antibody production. The sera was then tested for the ability to neutralize FeLV isolates. A five amino acid sequence within the gp70 coding region was determined to be required for neutralizing activity. The five amino acid epitope was the core of a number of short peptides to which antisera had been raised. The longest of these core peptides was 18 amino acids.

Nick, et al. (1990, J. Gen. Virol. 71: 77–83) synthesized 19 peptides, from 7–19 amino acid residues in length. These peptides were conjugated to keyhole limpit hemocyanin and the anti-peptide sera was tested for neutralizing ability against FeLV. One gp70 anti-peptide antibody involved in FeLV neutralization was raised against the peptide representing amino acids 221–227. This epitope is contained within a portion of the neutralization domain described by Nunberg, et al. (1990, Proc. Natl. Acad. Sci. USA 81: 3675–3679). However, anti-peptide antibodies raised against a peptide representing amino acids 228–234 of gp70, also contained within the Nunberg neutralization domain, did not neutralize FeLV in this study. The clustering of neutralization sites is located within a proline-rich sequence located between amino acids 230–289 of gp70 (Stewart, et. al., 1986, J. Virol. 58: 825–834; Donahue, et al., 1988 J. Virol. 62: 722–731).

A peptide vaccine providing initial protection against an FeLV challenge or as a booster to an initial vaccination against FeLV would be of immense value. A humoral response, cellular response and stimulation of an immunological memory would most likely result from a peptide retaining a secondary structure corresponding to the equivalent amino acid domain of an in vivo protein.

3. SUMMARY OF THE INVENTION

The present invention relates to peptide vaccines and methods of their use in providing initial prophylactic protection against FeLV challenge or as a booster to an initial vaccination to provide protection against FeLV challenge.

A peptide vaccine of the present invention is comprised of a plurality of proline residues aligned throughout the amino acid sequence such that the peptide substantially maintains an ordered, native-like secondary structure.

In a particular embodiment of the invention, the native-like structure in which the peptide folds is a polyproline beta turn helix. The peptide is induced to form a polyproline beta turn helix in part by comprising a percentage of proline residues ranging from about 10% to about 30%.

In a further embodiment of the invention, the peptide, which forms a polyproline beta turn helix, comprising a percentage of proline residues ranging from about 10% to about 30%, is at least about 80% homologous to the corresponding domain of the native protein at the amino acid level so as to induce a proper antibody response.

In yet a further embodiment of the invention, the peptide, which forms a polyproline beta turn helix by comprising a percentage of proline residues ranging from about 10% to about 30%, is at least about 80% homologous to the corresponding domain of a region from about amino acid 230 to about amino acid 290 of gp70 of feline leukemia virus.

In a preferred embodiment of the invention, the peptide, which forms a polyproline beta turn helix by comprising a percentage of proline residues ranging from about 10% to about 30%, is at least about 80% homologous to the corresponding domain of a region from about amino acid 230 to about amino acid 290 of gp70 of feline leukemia virus and is at least about 50 amino acids in length.

In an especially preferred embodiment of the invention, the peptide is PRN60 (SEQ ID NO:1).

In another embodiment of the invention, the peptide which forms a polyproline beta turn helix, comprising a percentage of proline residues ranging from about 10% to about 30%, is at least about 80% homologous to the corresponding domain of the native protein at the amino acid level so as to induce a proper antibody response and is formed via self assembly of two or more peptides.

In an additional embodiment of the invention, the peptide, which forms a polyproline beta turn helix by comprising a percentage of proline residues ranging from about 10% to about 30%, is at least about 80% homologous to the corresponding domain of the region from about amino acid 230 to about amino acid 290 of gp70 of feline leukemia virus and is formed via self assembly of two or more peptides.

In a preferred embodiment of the invention, the peptide, which forms a polyproline beta turn helix by comprising a percentage of proline residues ranging from about 10% to about 30%, is at least about 80% homologous to the corresponding domain of the region from about amino acid 230 to about amino acid 290 of gp70 of feline leukemia virus and is formed via self assembly of two or more peptides and is at least about 50 amino acids in length.

In an especially preferred embodiment of the invention, the peptide, is formed via self assembly of PRN42 (SEQ ID NO:2) and PRN4358 (SEQ ID NO:3).

The present invention also relates to methods of providing resistance against feline leukemia virus. A peptide is generated which comprises an amino acid sequence with a plurality of proline residues, the proline residues aligned throughout the amino acid sequence such that the peptide fragment substantially maintains a native-like structure. The peptide is isolated in a substantially pure form and utilized to vaccinate a susceptible host so as to provoke a humoral and cellular immune response as well as stimulating an immunologic memory.

In a particular embodiment of the invention, the peptide generated by the disclosed method folds into a polyproline beta turn helix. This peptide generated by the disclosed method is induced structurally to form a polyproline beta turn helix, comprising a percentage of proline residues ranging from about 10% to about 30%.

In a further embodiment of the invention, the peptide generated in the disclosed method, which forms a polyproline beta turn helix by comprising a percentage of proline residues ranging from about 10% to about 30%, is at least about 80% homologous to the corresponding domain of the native protein at the amino acid level so as to induce a proper antibody response.

In yet a further embodiment of the invention, the peptide generated in the disclosed method, which forms a polyproline beta turn helix by comprising a percentage of proline residues ranging from about 10% to about 30%, is at least about 80% homologous to a portion of the region from about amino acid 230 to about amino acid 290 of gp70 of feline leukemia virus.

In a preferred embodiment of the invention, the peptide generated in the disclosed method, which forms a polyproline beta turn helix by comprising a percentage of proline residues ranging from about 10% to about 30%, is at least about 80% homologous to the corresponding domain of the region from about amino acid 230 to about amino acid 290 of gp70 of feline leukemia virus and is at least about 50 amino acids in length.

In an especially preferred embodiment of the invention, the peptide generated in the disclosed method is PRN60 (SEQ ID NO:1).

In another embodiment of the invention, the peptide generated by the disclosed method, which forms a polyproline beta turn helix by comprising a percentage of proline residues ranging from about 10% to about 30%, is formed via self assembly of two or more peptides.

In an additional embodiment of the invention, the peptide generated by the disclosed method, which forms a polyproline beta turn helix by comprising a percentage of proline residues ranging from about 10% to about 30%, is at least about 80% homologous to the corresponding domain of the region from about amino acid 233 to about amino acid 289 of gp70 of feline leukemia virus and is formed via self assembly of two or more peptides.

In a preferred embodiment of the invention, the peptide generated by the disclosed method, which forms a polyproline beta turn helix by comprising a percentage of proline residues ranging from about 10% to about 30%, is at least about 80% homologous to the corresponding domain of the region from about amino acid 233 to about 289 of gp70 of feline leukemia virus and is formed via self assembly of two or more peptides and is at least about 50 amino acids in length.

In an especially preferred embodiment of the invention, the peptide of the disclosed method is generated via self assembly of PRN42 (SEQ ID NO:2) and PRN4358 (SEQ ID NO:3).

It is an object of the present invention to provide a vaccine, as a peptide, which provides initial protection against FeLV challenge or is given as a booster to an initial vaccination to provide protection against FeLV challenge.

It is also an object of the invention to provide this vaccine, as a peptide, which mimics the native-like structure of the corresponding domain of the native protein so as to stimulate a prolonged immune response.

It is a further object of the invention to provide this vaccine, as a peptide, forming a polyproline beta turn helix in solution, thus mimicking the native-like structure of the corresponding domain of the native protein so as to stimulate a prolonged immune response.

It is an object of the present invention to provide this vaccine, as a peptide, which forms a polyproline beta turn helix in solution and is at least about 80% homologous at the amino acid level to a portion of the region from about amino acid 233 to about amino acid 289 of gp70 of feline leukemia virus.

It is an object of the present invention to provide this vaccine in the form of PRN60 (SEQ ID NO:1).

It is also an object of the present invention to provide this vaccine as a peptide formed via self assembly of PRN42 (SEQ ID NO:2) and PRN4358 (SEQ ID NO:3).

It is an object of the present invention to provide a method of initial vaccination against FeLV challenge or a booster to an initial vaccination to provide protection against FeLV challenge utilizing one or more of the peptides disclosed within this specification.

It is also an object of the present invention to provide a method of promoting susceptible host protection against FeLV infection comprising use of the PRN60 peptide vaccine, introduced into the susceptible host in either a modified or unmodified form such that the peptide vaccine induces a humoral and cellular response upon vaccination of the susceptible host.

Is it also an object of the present invention to provide a method of promoting susceptible host protection against FeLV infection comprising use a peptide vaccine formed via self-assembly of two peptides such that the peptide vaccine, introduced into the susceptible host in either a linked or unlinked form, induces a humoral and cellular response upon vaccination of the susceptible host.

These and other objects of the invention will be more fully understood from the following description of the invention and disclosed examples, the referenced figures and tables attached hereto and the claims appended hereto.

3.1 Definitions

The terms listed throughout this specification will have the meanings indicated.

FeLV—Feline Leukemia Virus
CTL—Cytotoxic T—Lymphocyte
DPI—Days Post Infection
UVD—Unintegrated Viral Deoxyribonucleic Acid
HIV—Human Immunodeficiency Virus
EIAV—Equine Infectious Anemia Virus
LTR—Long Terminal Repeat
PLL—Poly-L-Lysine
KHL—Keyhole Limpit Hemocyanin

4. BRIEF DESCRIPTION OF THE FIGURES

Figure 1B:
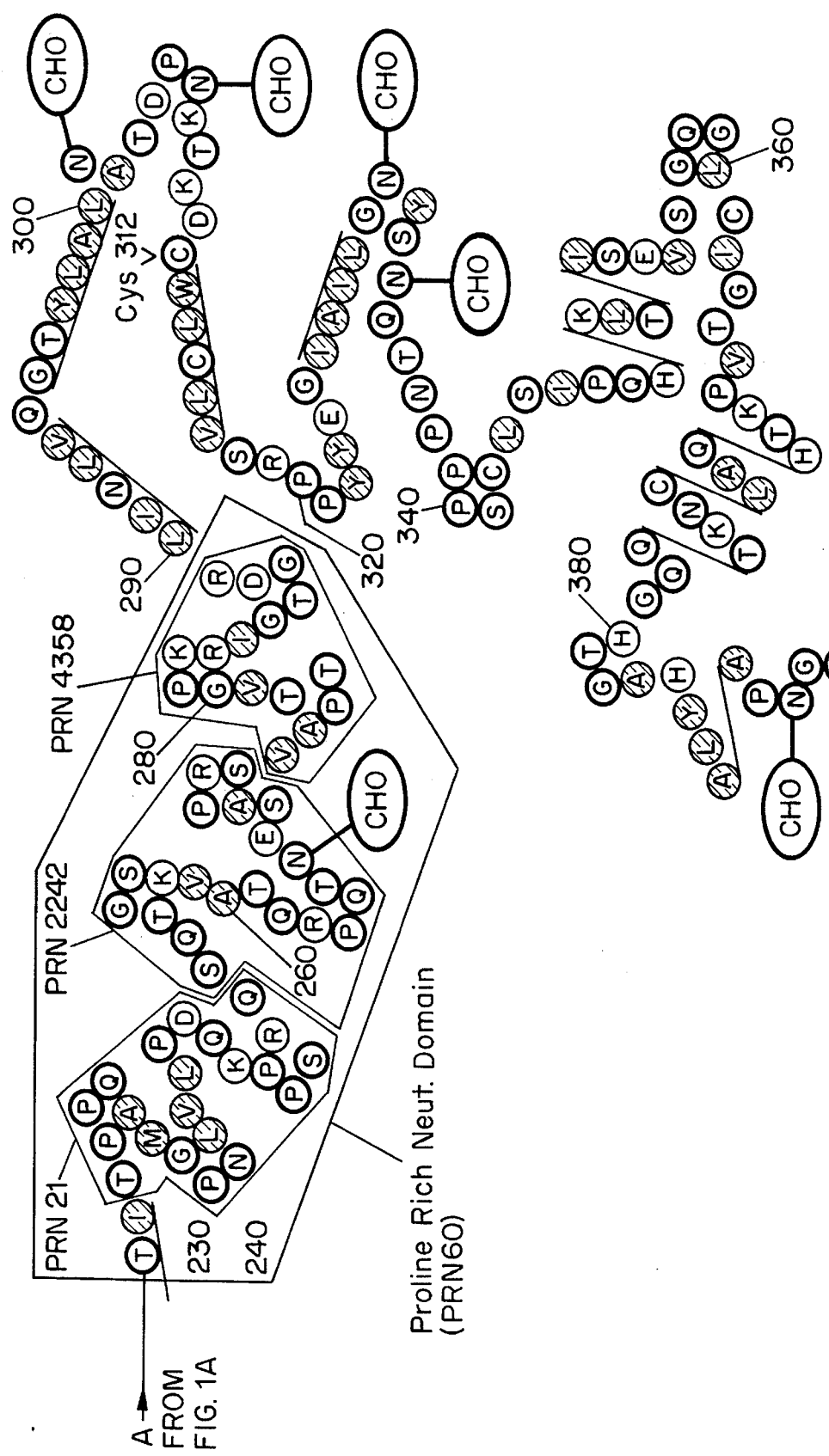
Figure 1C:
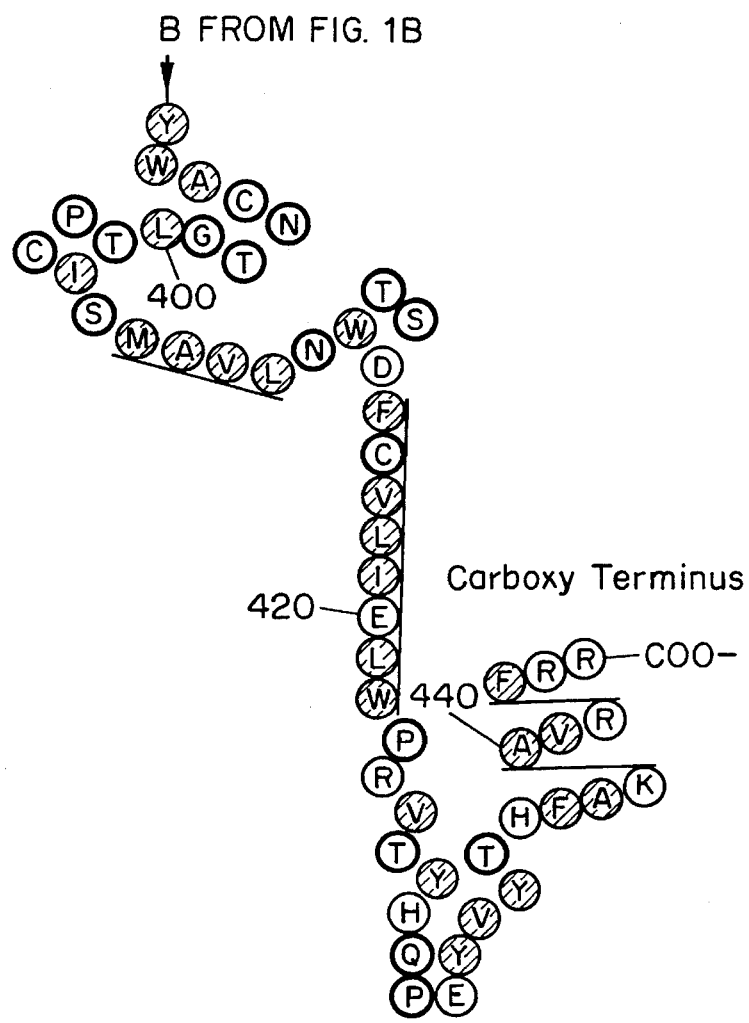
Figure 1C:
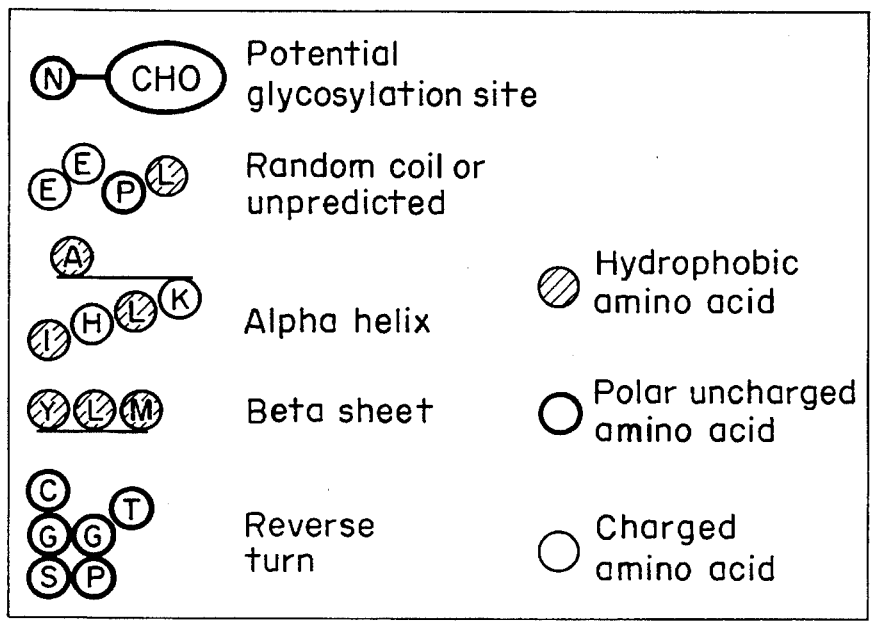

FIGS. 1A–C illustrate a computer model of the amino acid primary and secondary structure of FeLV gp70 (SEQ ID NO:6).

Figure 2:
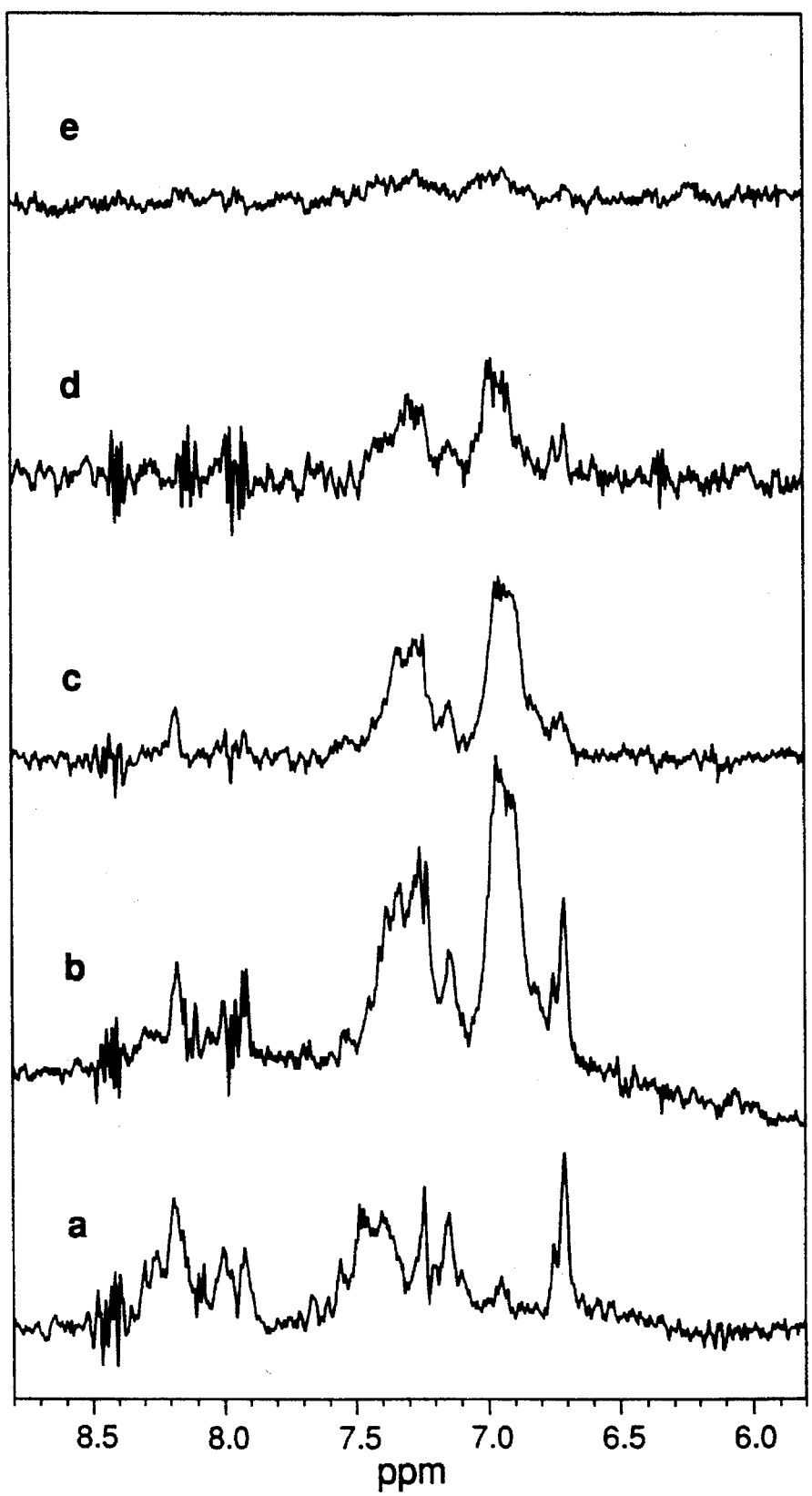

FIG. 2 illustrates the 500-MHz spectra $^1$H-NMR of PRN60 peptide fragments dissolved in deuterated 0.1M phosphate buffer pH 7.2, in $D_2O$. (a) PRN60, (b) N-terminal 42 amino acids (PRN42), (c) N-terminal 21 amino acids (PRN21), (d) central 20 amino acid fragment (PRN2242), (e) C-terminal 16 amino acid fragment (PRN4358).

Figure 3:
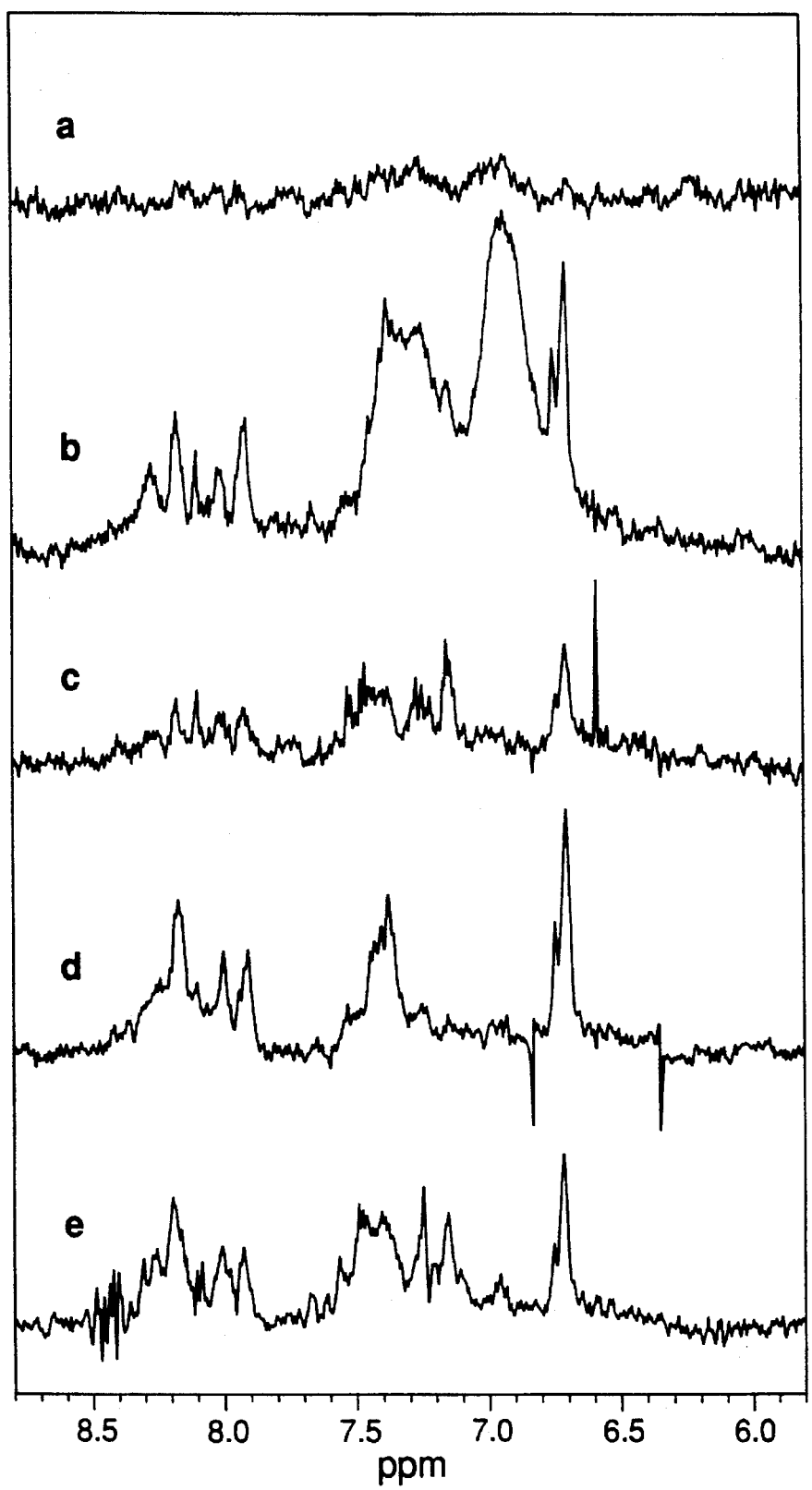

FIG. 3 illustrates the 500-MHz spectra $^1$H-NMR of PRN peptides dissolved in deuterated 0.1M phosphate buffer pH 7.2, in $D_2O$. (a) C-terminal 16 amino acid fragment (PRN4358), (b) N-terminal 42 amino acids (PRN42), (c) PRN42+PRN4358 dissolved in $1H_2O$, phosphate buffer followed in solution exchange into $D_2O$, phosphate buffer, (d) PRN42+PRN4358 dissolved into $D_2O$, phosphate buffer, (e) PRN60.

Figure 4:
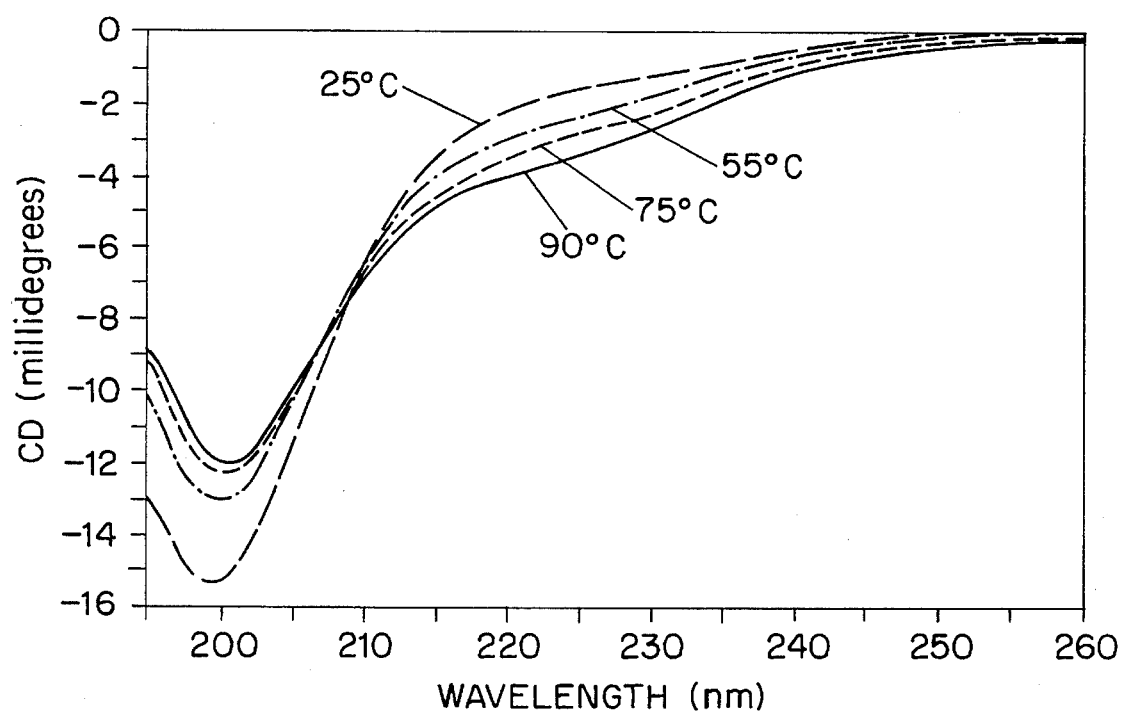

FIG. 4 illustrates the circular dichroism spectrum of PRN60 in 0.01M phosphate buffer, pH 7.2.

5. DETAILED DESCRIPTION OF THE INVENTION

The present invention relates to peptide vaccines and methods of their use in providing initial protection against FeLV challenge or as a booster to an initial vaccination to provide protection against FeLV challenge.

Peptide vaccines are disclosed which elicit a humoral and cellular immune response in experimental vaccinations against host exposure to feline leukemia virus. These peptide vaccines comprise an amino acid sequence with a plurality of proline residues, the proline residues aligned throughout the amino acid sequence such that the peptide fragment substantially maintains a native-like structure. As discussed in the Background of the Invention, synthetic peptides for the most part have historically been unable to substantially maintain the native-like secondary structure in solution, thus limiting their usefulness as vaccines. However, the present invention discloses a synthetic peptide containing a plurality of proline residues synthesized to a surprising length and purity, these peptides shown to substantially maintain the ordered secondary structure of the corresponding protein domain in solution.

In a particular embodiment of the invention, the native-like structure in which the peptide folds is a polyproline beta turn helix. The peptide is induced to form a polyproline beta turn helix by comprising a percentage of proline residues ranging from about 10% to about 30%.

In a further embodiment of the invention, the peptide, which forms a polyproline beta turn helix, comprising a percentage of proline residues ranging from about 10% to about 29%, is at least about 80% homologous to the corresponding domain of the native protein at the amino acid level so as to induce a proper antibody response.

In another embodiment of the invention, the peptide vaccine, comprising from about 10% to about 30% proline residues; and at least about 80% homologous to the corresponding protein domain; is at least about 50 amino acids in length.

Several embodiments of the invention are disclosed through the synthesis, isolation and utilization of peptides corresponding to at least a portion of the proline-rich neutralization domain of FeLV gp70. The envelope glycoproteins of FeLV were modeled according to the rules of Chou and Fasman (1978, Ann. Rev. Biochem. 47: 251–276), as well as considering amphipathic character (Margalit, et al., J. Immunol. 138: 2213–2229) and surface potential (Parker, et al., 1986, Biochemistry 25: 5425–5431) of the proteins sequence. The experimentally determined structural model of the FeLV 61-E gp70 protein (hereinafter referred to as gp70) is disclosed in FIG. 1 (gp70 is SEQ ID NO:6). This model indicates a domain of the gp70 amino acid sequence consisting of 10 sequential reverse turns which is rich in proline residues and determined experimentally to form a polyproline beta turn helix.

In one embodiment of the invention, a peptide synthesized from at least a portion of this gp70 coding region, from about amino acid 233 to about amino acid 289 (FIG. 1) maintains an ordered, native-like secondary structure.

This embodiment of the invention is exemplified, but not limited to, the peptide PRN60 as a vaccine against FeLV challenge. The PRN60 peptide spans amino acid 230–290 of the gp70 amino acid sequence (FIG. 1). The PRN60 peptide vaccine may be generated by a number of known procedures, including but not limited to automated peptide synthesis, manual peptide synthesis or by controlled digestion of peptide fragments. This peptide vaccine is then isolated in a substantially pure form, substantially maintaining an order structure in solution. The present invention discloses a conformational model of gp70 and the region represented by PRN60 has been predicted to consist of sequential reverse turns. This peptide contains 18% proline, 11% threonine, 9% serine, and 9% glycine and 9% glutamine. This sequential reverse turn motif predicted by our model is consistent with the polyproline beta turn helix form of secondary structure associated with proline-rich repeat sequences. NMR spectroscopy measurement of intrinsic viscosity, as well as determining the circular dichroism spectrum of PRN60 has been utilized to determine that this peptide retains a highly ordered confirmation in solution. Therefore, it is disclosed in the present invention that PRN60 forms an ordered structure in solution with large confirmation mobility that is long lived, and that peptide fragments of this structure will self assemble into the native-like confirmation experimentally predicted in the model depicted in FIG. 1. The PRN60 peptide was utilized to immunize cats, mice and rabbits with both free peptide and carrier bound peptide. As discussed further in Example Section 7, PRN60 induces both humoral and cellular immune responses that may protect against FeLV infection. Therefore, it is disclosed by way of example, and not of limitation, that an extremely long peptide corresponding to a domain of gp70, experimentally predicted by computer modeling to possess a polyproline beta turn helix region, both retains that structure as well as inducing in both humoral and cellular immune responses subsequent to vaccination of a susceptible host.

In an additional embodiment of the invention, the peptide, which forms a polyproline beta turn helix by comprising a percentage of proline residues ranging from about 10% to about 30%, is at least about 80% homologous to a portion of the region from about amino acid 230 to about amino acid 290 of gp70 of feline leukemia virus and is formed via self assembly of two or more peptides.

In a preferred embodiment of the invention, the peptide, which forms a polyproline beta turn helix by comprising a percentage of proline residues ranging from about 10% to about 30%, is at least about 80% homologous to a portion of the region from about amino acid 230 to about amino acid 290 of gp70 of feline leukemia virus and is formed via self assembly of two or more shorter peptides and is at least about 50 amino acids in length.

In still another embodiment of the invention, two or more peptide fragments are mixed to self-assemble into a larger peptide fragment. It is disclosed that smaller peptides corresponding to sub-regions of the PRN60 domain do not share secondary structural characteristics with PRN60. These smaller peptides self-assemble into a larger peptide fragment in vitro. The self-assembly of these smaller peptides results in a larger peptide with an ordered, native-like secondary structure similar to PRN60. In a specific embodiment of the invention, the peptide fragment PRN42 (Table 2; SEQ ID NO:2) is mixed with the peptide fragment PRN4358 (Table 2; SEQ ID NO:5). These two peptide fragments self-assemble into a peptide fragment exhibiting secondary structural characteristics substantially similar to PRN60. Therefore, smaller peptides may be utilized to construct the extremely long, structurally ordered peptides (such as PRN60) to be utilized as vaccines.

The present invention also relates to methods of providing resistance against feline leukemia virus. A peptide is generated which comprises an amino acid sequence with a plurality of proline residues, the proline residues aligned throughout the amino acid sequence such that the peptide fragment substantially maintains a native-like structure. The peptide is isolated in a substantially pure form and utilized to vaccinate a susceptible host so as to provoke a humoral and cellular immune response as well as stimulating an immunologic memory.

In a particular embodiment of the invention, the peptide generated by the disclosed method folds into a polyproline beta turn helix. This peptide generated by the disclosed method is induced to form a polyproline beta turn helix, comprising a percentage of proline residues ranging from about 10% to about 30%.

In a further embodiment of the invention, the peptide generated in the disclosed method, which forms a polyproline beta turn helix by comprising a percentage of proline residues ranging from about 10% to about 30%, is at least about 80% homologous to the corresponding domain of the native protein at the amino acid level so as to induce a proper antibody response.

In yet a further embodiment of the invention, the peptide generated in the disclosed method, which forms a polyproline beta turn helix by comprising a percentage of proline residues ranging from about 10% to about 30%, is at least about 80% homologous to the corresponding domain of the region from about amino acid 230 to about amino acid 290 of gp70 of feline leukemia virus.

In a preferred embodiment of the invention, the peptide generated peptide in the disclosed method, which forms a polyproline beta turn helix by comprising a percentage of proline residues ranging from about 10% to about 30%, is at least about 80% homologous to the corresponding domain of the region from about amino acid 230 to about amino acid 290 of gp70 of feline leukemia virus and is at least about 50 amino acids in length.

In an especially preferred embodiment of the invention, the peptide generated in the disclosed method is PRN60 (SEQ ID NO:1).

In an additional embodiment of the invention, the peptide generated by the disclosed method, which forms a polyproline beta turn helix by comprising a percentage of proline residues ranging from about 10% to about 30%, is at least about 80% homologous to a portion of the region from about amino acid 230 to about amino acid 290 of gp70 of feline leukemia virus and is formed via self assembly of two or more peptides.

In a preferred embodiment of the invention, the peptide generated by the disclosed method, which forms a polyproline beta turn helix by comprising a percentage of proline residues ranging from about 10% to about 30%, is at least about 80% homologous to a portion of the region from about amino acid 230 to about 290 of gp70 of feline leukemia virus and is formed via self assembly of two or more peptides and is at least about 50 amino acids in length.

In an especially preferred embodiment of the invention, the peptide of the disclosed method is generated via self assembly of PRN42 (SEQ ID NO:2) and PRN4358 (SEQ ID NO:3).

The peptide vaccines utilized in accordance with this invention may be prepared by methods other than manual or automated peptide synthesis. By way of example and not of limitation, the peptides may be prepared by peptide isolation, such as the controlled enzymatic digestion of the proline-rich region of the FeLV-gp70 transmembrane protein, followed by purification of the peptide fragment in a substantially pure form. Alternatively, the amino acid sequence comprising this envelope peptide may be encoded as a portion of a larger peptide sequence, the larger peptide sequence having been expressed by recombinant DNA techniques known to one of ordinary skill in the art.

It also will be well known to one of ordinary skill in the art that a susceptible host may be immunized using the appropriate peptide vaccine formulated in adjuvant to increase the immune response. Such adjuvants include but are not limited to Freund's (complete and incomplete), mineral gels, such as aluminum hydroxide, surface active substances such as keyhole limpet hemocyanin, lysolecithin, pluronic polyols, polyanions, peptides, BCG (Bacille Calmette-Guerin), oil emulsions and dinotrophenols. Immunization can be carried out with additional various presentation and cross-linking permutations. By way of example and not of limitation, such permutations include PRN60 crosslinked to KLH as a carrier, PRN60 cross-linked to FeLV core protein as carrier, PRN60 cross-linked to itself, and these combinations presented by the various adjuvants listed above. It will become evident that such permutations are available in regard to other peptides and self-assembled peptides disclosed throughout this specification.

It will also be known to one of ordinary skill in the art that use of the term "susceptible host" includes any such mammalian host susceptible to infection by feline leukemia virus. It will be further evident that any such susceptible host is a candidate for treatment to promote protection from FeLV utilizing the peptide vaccines and associated methods described in this specification. A primary target for treatment utilizing these peptide vaccines and associated methods are cats, with primary emphasis on treating domestic cats.

The following examples are offered by way of illustration of the present invention, and not by way of limitation.

6. EXAMPLE: A PROLINE RICH NEUTRALIZATION DOMAIN OF FeLV SURFACE UNIT PROTEIN (gp70) FORMS A POLYPROLINE β-TURN HELIX SECONDARY MOTIF

6.1. Materials and Methods

6.1.2. Peptide Synthesis

Synthetic peptides were prepared by a manual solid-phase strategy using 9-fluorenylmethyloxycarbonyl protected amino acids. Dimethylformamide (DMF) was sequencing grade from FisherBiotech (Fairlawn, N.J.). TFA was sequencing grade from MilliGen/Biosearch, Div. of Millipore (Burlington, Mass.). Thioanisole (TA), ethanedithiol (EDT) and Hobt were peptide synthesis grade and purchased form DuPont (Boston, Mass.). Methanol, dichloromethane (DCM), acetonitrile and toluene were HPLC grade and purchased from Mallinkrodt (Paris, Ky.).

The techniques for producing, purifying and characterizing peptides are described in Fontenot, et al. (1991, Peptide Research 4: 19–25). Briefly, peptides were synthesized by a manual solid-phase method using 9-fluorenylmethoxycarbonyl (Fmoc) protected amino acids. Fmoc amino acid side-chain protecting groups include t-butyl ethers for serine, threonine, tyrosine, aspartic acid, and glutamic acid; cysteine t-butyl or trityl for cysteine; Boc for lysine; 4-methoxy-2,3,6-trimethylbenzenesulfonyl (Mtr) and N-(2,2,5,7,8-penthamethyl) chroman-6-sulfonyl (PMC) for arginine; and trityl for histine. The resulting synthetic peptides were deprotected and cleaved from the resin support in trifluoroacetic acid with the appropriate scavengers, followed by sequential extractions with organic solvents and purification by conventional gel filtration and reverse phase HPLC. Molecular weight analysis of the purified peptide was performed using electrospray mass spectroscopy.

Briefly, peptides were synthesized manually on a Rapid Multiple Peptide Synthesizer (RaMPS) from DuPont. The syntheses were performed in groups of 5–10 peptides utilizing 0.1 mM Rapid Amine (2,3-dimethoxybenzhydrylamine resin) cartridges from DuPont which yield C-terminal amides. The standard coupling procedure was performed using 0.25 mmol preformed pentafluorophenyl esters of fluorenylmethoxycarbonyl amino acids (Fmoc-AA-opfp) and 0.1 mmol of Hobt in 3 ml DMF. The coupling times were a standard 2 h, followed by extensive DMF and methanol washes. The completeness of the coupling reaction was monitored by the method of Kaiser et al. (1970, Anal. Biochem. 34: 595–598). The Kaiser reagents were purchased from DuPont. Exceptions to the standard opfp ester activation coupling include alanine, histidine, arginine and trityl-protected cysteine, which were each coupled as the symmetric anhydride. Cysteine was also coupled as a Hobt ester for t-butyl-protected cysteine. Serine and threonine were coupled as 3-hydroxy-4-oxo-3,4 dihydrobenzotriazine (odhbt) esters purchased from DuPont.

Upon completion of the synthetic regimen, the resins were deblocked in 3 ml of 50:50 DMF:piperidine for 9 minutes, followed by extensive washing in DMF and methanol. Following the final methanol wash, the resin was air-dried by suction for 10 minutes. Final TFA cleavage and deprotection were performed by the manufacturer's suggested procedures. Briefly, Arg-containing peptides were shaken vigorously for 16 hours in a solution of 90% TFA, 5% EDT, 4% water and 1% TA. Peptides without Arg were cleaved in a solution of 90% TFA, 5% EDT and 5% water. Finally the TFA was evaporated, and the peptides were extracted sequentially with ethyl ether, ethyl acetate and water, followed by lyophilization.

Automated peptide synthesis may be performed with a MilliGen/Biosearch SAM II peptide synthesizer according to manufacturer-specified protocols. Briefly, peptides are synthesized on Fmoc-L-amino acid-p-benzyloxybenzyl alcohol resins generating C-terminal acids. Amino acids are activated by the addition of 0.4M diisopropylcarbodiimide (DIC) in the presence of equimolar Hobt and amino acid. Coupling times are a standard 1 hours. Exceptions include opfp ester activation of asparagine and glutamine, and symmetric anhydride for leucine. Deblocking is performed in a solution of 30% piperidine in 50:50 toluene:DMF for 3.15 minutes. Final cleavage is performed in a solution of TFA:TA:EDT:anisole at a ratio of 90:5:3:2 for 8 hours with Arg-containing peptides. Final cleavage for peptides without Arg and Trp is in a solution of TFA:DCM:DMS at a ratio of 70:25:5 for 2 hours. Peptides with Trp, but without Arg, are cleaved in a solution of TFA:DCM:indole at a ratio of 70:28:2.

6.1.3. NMR Spectroscopy

All peptides samples for NMR analysis were prepared from HPLC purified and lyophilized peptide. The sample concentrations were all 5 mM in 0.1M phosphate buffer pH 7.2 with either 90%/10%, $H_2O/D_2O$ or 99.5% $D_2O$. High ionic strength buffer was used to reduce the electrostatic interactions. A pH of 7.2 was chosen to approximate native conditions and to maximize the rate of proton exchange into $D_2O$, thereby insuring that only the most long-lived protons would be present when the $^1$H-NMR spectra were recorded.

The NMR spectra were recorded on a Bruker AM-500 spectrometer equipped with an Aspect 3000 computer and a 5-mm $^1$H probe. The temperature of the probe was regulated with a BVT-1000 unit and calibrated with a sample of methanol. The spectra in $D_2O$ were obtained 5–10 minutes after dissolution of the peptides. The water signal was suppressed during the repetition delay of 1.5 seconds for samples in $H_2O$ and $D_2O$. A control spectrum of the $D_2O$ sample was taken without water pre-saturation to make sure that none of the amide protons are affected by pre-saturation of water at any given power level. A total of 1024 transients were collected for each spectrum. The proton chemical shift is referred to the proton resonance of 2,2-dimethyl-2-silapentane-5-sulfonate (DSS) at 0.0 ppm.

6.1.4. Circular Dichroism

Circular dichroism spectra were recorded on a Jasco model J-710 spectropolarimeter equipped with a PTC-343 peltier-type thermostatic cell holder and temperature control program. The spectra were recorded from 195–260 nm, with readings every 0.1 nm. The peptide concentrations were 0.1 mg/ml of HPLC purified peptide in 0.01M phosphate buffer at pH 7.2. A 0.1-cm path length strain free quartz cuvette was used for all measurements.

6.1.5. Intrinsic Viscosity

Viscometry measurements were performed in a Cannon-Fenske-Ostwald type capillary viscometer using HPLC purified peptide in 0.1M phosphate buffer at pH 7.0 and 30° C. The procedure used was as described by Tanford & Buzzell (1956, J. Phys. Chem. 60: 225–231) and Buzzell & Tanford (1956, J. Phys. Chem. 60:1204–1207). The capillary constant was calculated as described by Tanford & Buzzell (1956, J. Phys. Chem. 60: 225–231). All kinematic viscosity measurements were repeated at least ten times and the averages used to calculate the intrinsic viscosity. Intrinsic viscosity was calculated from kinematic viscosity and the appropriate density correction (0.0029 ml/g) was applied as described by Tanford (1955, J. Phys. Chem. 59: 798–799). The Simha shape factor and the peptide axial ratios were calculated as described Tanford (1961, In: Physical chemistry and macromolecules. John Wiley and Sons, New York, N.Y. pp 390–405) and Cantor & Schimmel (1980, Biophysical Chemistry. Part 2: Techniques for the Study of Biological Structure and Function: W. H. Freeman and Co, New York, N.Y.).

6.1.6. Molecular Modeling

Potential structural domains of the surface unit protein of gp-70 (Stewart, et al., 1986, J. Virol. 58 825–834; Overbaugh, et al., 1988, Science 239: 906–910) was determined experimentally through the use of various models utilized to calculate secondary structure (Chou and Fasman, 1978, Ann. Rev. Biochem 47:251–276); surface potential (Parker, 1986, Biochemistry 25: 5425–5431) and amphipathic alpha helical regions (Margalit et al., 1987, J. Immunol. 138: 2213–2229).

The sequence of PRN60 was modeled into a poly type I turn conformation on a Silicon Graphics model INDIGO (Mountain View, Calif.) terminal using the Tripos molecular graphic program Sybyl (St. Louis, Mich.). From this model, the distance of the longitudinal axis and cross sectional axis were estimated.

6.2. Results and Discussion

6.2.1. Molecular Model of gp70-PRN60

While experimentally constructing a conformational model of gp70 an unusual sequence was detected spanning amino acids 230–289 that was predicted to consist of 10 sequential reverse turns (Table 1). This peptide segment is 18% proline, 11% threonine, 9% serine, 9% glycine and 9% glutamine and appears to be a mucin-like sequence (Jentoft, 1990, Trends Biochem Sci. 15: 291–294; Strouss and Dekker, 1992, Critical Review in Biochemistry and Molecular Biology 27: 1/2:57–92). This segment contains disclosed neutralizing sites for FeLV and has been designated the proline-rich neutralization domain. The proline-rich sequence is entirely incompatible with either α-helix or β-sheet secondary structure by Chou-Fasman analysis. The pattern of (PXXV)A(PXXV)G(PXXI) appears in amino acids 271–289 and (PXXV) again at amino acids 239–242 of FeLV gp-70E, with XX being two hydrophilic amino acids. Six of the potential turns are predicted with a probability greater than twice the value necessary to predict a turn, and all ten proposed turn sequences have a turn conformational potential ($P_t$) greater than 1.00 and $P_t$ greater than $P_\alpha$ of $P_\beta$.

In addition, there are no aromatic amino acids within this domain. The 13 amino acids N-terminal (219–310) to PRN60 and 12 amino acids C-terminal (290–301) are predicted to be β-sheet. There are no cysteines within either PRN60 or the flanking β-sheet regions. The nearest cysteines to the proline-rich sequence are cys 185 and cys 312. The lack of cysteine residues is in distinct contrast to the approximately 180 residues at the N-terminus and C-terminus of gp70, each with 8 cysteine residues. In total there are 8 cysteines in the N-terminal 185 amino acids and 8 cysteines from amino acid 312 through 445. This arrangement may result in the entire proline-rich domain with flanking β-sheets forming an exposed loop structure in the native gp70 molecule.

The sequential reverse turn motif formulated by our modeling is consistent with the polyproline, β-turn helix form of secondary structure associated with the proline-rich repeat sequences of proteins as proposed by Matsushima et al. (1990, Proteins: Structure, Function and Genetics 7: 125–155). In the present disclosure, the predicted structural motif of the FeLV proline-rich sequence is evaluated directly using $^1$H-NMR and CD spectroscopy as well as measurements of intrinsic viscosity.

6.2.2. Peptides

The PRN peptides that were synthesized are summarized in Table 2. These include the entire 60 amino acid region (PRN60) taken from FeLV gp70 amino acids 230–289, the N-terminal 42 amino acids (PRN42), the N-terminal 21 amino acids (PRN21), the middle 20 amino acids (PRN2242) and the C-terminal 16 amino acids (PRN4358). The molecular weights of the peptides were confirmed by electrospray mass spectroscopy, and in each case the molecular weight obtained was the expected weight.

6.2.3. NMR Spectroscopy $^1$H-NMR spectroscopy was chosen to investigate the folded state of the PRN peptides. In this study, the test peptides were dissolved in deuterated phosphate buffer in $D_2O$ and the region of the $^1$H-NMR spectrum that is characteristic of amide protons was monitored for protected protons. The occurrence of amide proton resonances in $D_2O$ indicates that the peptide is folded into a compact structure in which amides are buried and inaccessible to solvent $D_2O$ molecules.

The $^1$H-NMR spectrum of each PRN peptide was determined in 0.1M phosphate buffer, pH 7.2 in 90%/10%, $H_2O/D_2O$, and in 0.1M deuterated phosphate buffer, pH 7.2 in 99.9% $D_2O$. The results of the peptides dissolved in $D_2O$ are shown in FIG. 2. The amide proton region of the $^1$H-NMR spectrum reveals that there are protons protected from exchange with $D_2O$ in each of the peptides except the C-terminal 16 amino acid peptide. This indicates that the peptide forms a folded structure in solution and that there are amide protons which are stable and protected from solvent. Many of the features of the $^1$H-NMR spectrum of the 60 amino acid peptide (PRN60; FIG. 2*a*) are distinct from the pattern seen in the 2 twenty amino acid peptides PRN21 (FIG. 2*c*) and PRN2242 (FIG. 2*d*), most noticeably the large resonance at 6.9 ppm is absent in the 60-mer and is present in the $D_2O$ spectrum of the two 20-mers. The resonances in the spectrum of PRN60 from 7.1 to 7.6 ppm are present but shifted and less complex in the two 20-mers. In addition, the sixty amino acid peptide shows a complex series of resonances from 7.9 to 8.4 ppm that are absent in the two 20-mers. The $^1$H-NMR spectrum is $D_2O$ of the peptide corresponding to the N-terminal 42 amino acids (FIG. 2*b*) of PRN60 contains resonances similar to both the 60 amino acid peptide $^1$H-NMR spectrum and the two twenty amino acid peptide $^1$H-NMR spectra. The spectrum of the 42 amino acid peptide contains a broad resonance at 6.9 ppm which is present in PRN21 (FIG. 2c) and PRN2242 (FIG. 2d). However, the spectrum of the 42 amino acid peptide also contains a series of resonances from 7.9 to 8.4 ppm, that are not as complex as that seen in the spectrum of the 60 amino acid peptide in D$_2$O and yet are absent in the spectrum of the two 20 amino acid peptides. The $^1$H-NMR spectrum in D$_2$O of the C-terminal segment (PRN 4358; FIG. 2e) does not show any protection of protons alone in D$_2$O, indicating the lack of significant conformation in this particular peptide. The line-widths of the proton resonances increase as the frequency increases and as the peptide size decreases. This indicates that there is a large conformational mobility for PRN60 and the mobility increases for the peptide fragments (Chaffotte, et al., 1991, Biochemistry 30: 8067–8074).

The resonances seen in PRN60, PRN21, and PRN2242 in D$_2$O were followed for three days and decreased in intensity only slightly when kept at 4° C. in between measurements. Upon heating the PRN60 in D$_2$O sample to 4° C., and equilibrating for one hour, there was a significant decrease in intensity of the resonances from 7.9 to 8.4 ppm and in the two peaks in between 6.7 and 6.8 ppm. The series of resonances from 7.1 to 7.6 ppm were remarkably stable to increased temperature, even 60° C. for 12 hours failed to completely allow exchange of these protons. The effect of increased temperature on the $^1$H-NMR spectrum of PRN60 in the region of 0.0 to 5.0 ppm was to sharpen the lines of the alpha-, beta-, and gamma-proton resonances indicating that the side chains of the amino acids are exposed to the solvent and not buried in a globular fold. Increasing the temperature of 60° C. in the presence of 6M urea caused multiple shifts of resonances in the region of the alpha and beta protons indicating an unfolding process was occurring. These results demonstrate that the PRN peptide sequences assume a high ordered stable secondary structure compatible with a polyproline β-turn helix.

6.2.4. Self-Assembly of PRN Peptides

The N-terminal 42 amino acid peptide (PRN42) and the C-terminal 16 amino acid peptide (PRN4358) self assemble into some state approaching the native fold when mixed together. When an equimolar (5 mM) amount of PRN4358 (FIG. 3a) is mixed with PRN42 (FIG. 3b) in H$_2$O, followed by exchange into D$_2$O, the result is the native-like $^1$H-NMR spectrum seen in FIG. 3c. The NMR spectrum of the mixture (FIG. 3c) indicates that the peptides form a complex that is very similar to that of PRN60. The most striking feature of the NMR spectrum of the self assembled mixture is the complete loss of the largest peak associated with the 42 amino acid peptide at 6.9 ppm. This peak at 6.9 ppm which is present in PRN21, PRN2242, and PRN42 is the most distinguishing difference between the spectrum of these peptides and the spectrum of the 60 amino acid peptide. In addition, the large band of resonances from 7.2 to 7.6 ppm present in the $^1$H-NMR spectrum of the 42 amino acid peptide is replaced by a complex series of sharper peaks which are similar to the pattern seen in the spectrum of PRN60. A similar result is obtained if the two peptides are mixed in H$_2$O, is allowed to equilibrated for 2 hours, followed by freezing and lyophilization before dissolution in D$_2$O (FIG. 3d). Again, the large peak at 6.9 ppm which is characteristic of the 42 amino acid peptide is completely absent in the $^1$H-NMR spectrum of the mixture (FIG. 3d). The NMR spectrum of the region from 7.2 to 7.6 ppm is intermediate in spectral detail when compared to PRN60 (FIG. 3e) and PRN42 (FIG. 3b) in the lyophilized sample. However, the details of the NMR spectrum from 7.9 to 8.4 ppm more closely resemble PRN60 when the sample is lyophilized. Thus, these NMR data indicate that synthetic peptide segments of the proline-rich domain can self-assemble into complex ordered multimers with the structure of the full length PRN60 peptide. The propensity for self-assembly in proline-rich repetitive proteins is compatible with a β-turn helix structure, as described for the dynamic β-spirals of bovine elastin (Urry, 1987, J. Prot. Chem. 7: 1–34). In the case of elastin, the sequence (VPAVG)n forms repeating type II β-turns (Bhandary, et al., 1990, Int. J. Peptide Protein Res. 36: 122–127). The repetitive turn motif of elastin displays some very unusual physical properties such as: (i) self-assembly to form fibrils, (ii) increasing order with increasing temperature up to 60° C., and (iii) development of viscoelastic force coincident with molecular ordering (Urry, 1987, J. Prot. Chem. 7: 1–34; Urry, et al., 1988, Proc. Natl. Acad. Sci: USA 85: 3407–3411).

6.2.5. Intrinsic Viscosity

The intrinsic viscosity of a protein is exquisitely sensitive to the folded state and shape of a protein (Tanford, 1961, In: *Physical Chemistry and Macromolecules*; John Wiley and Sons, New York, N.Y.; 390–405; Tanford, et al., 1967, J. Am. Chem. Soc. 89: 729–736). The intrinsic viscosity is extrapolated from the reduced viscosity at zero concentration and that value is 7.49 ml/g for PRN60 (Table 3). Tanford has shown that the intrinsic viscosity of a protein in the random coil state is the highest viscosity state achievable and is given by the equation $[\eta]=0.716$ (n) 0.66, where n is the number of residues in the protein. The theoretical value of $[\eta]$ calculated for PRN60 in a random coil state is 10.7 ml/g. The measured value of $[\eta]$ for PRN60 was determined to be 7.49 ml/g (Table 3). This measured value is significantly less than the theoretical intrinsic viscosity predicted for random coil 60 amino acid peptide. In fact, the $[\eta]$ value of 7.49 ml/g predicts a random coil peptide of 36 amino acid residues. The relatively low intrinsic viscosity for the PRM peptide indicates a highly ordered conformation for this peptide in solution. This result agrees with the $^1$H-NMR experiments indicating that PRN60 forms a folded structure PRN in solution.

Intrinsic viscosity measurements also provide information on the shape of macromolecules. The values of intrinsic viscosity obtained for spherical, globular proteins are in the range of 3.3 to 3.9 ml/g and are independent of molecular weight (Tanford, 1961, In: *Physical Chemistry and Macromolecules*; John Wiley and Sons, New York, N.Y.; 390–405). The value of 7.49 ml/g for the intrinsic viscosity of PRN60 is inconsistent with a globular folded state for this molecule. However, this value is consistent with a prolate ellipsoid shape of axial ratio equal to 9.1 (Table 3) (Cantor & Schimmel, 1980, In: *Biophysical Chemistry*; Part 2: Techniques for the Study of Biological Structure and Function. W. H. Freeman and Co, New York, N.Y.). This value for the axial ratio is in good agreement with the value of 9.7 (longitudinal axis/cross sectional axis) obtained from a computer model of this sequence in a poly-type I turn secondary structural motif.

6.2.6. Circular Dichroism

The circular dichroism spectrum of PRN60 in 0.01M phosphate buffer at 25° C. is shown in FIG. 4. The spectrum reveals a characteristic large negative peak with a minimum at 198 nm (FIG. 4). The shape of the spectrum was unaffected by increasing the temperature sequentially to 55° C., 75° C. and 90° C. (FIG. 4). However, the intensity at 198 nm decreased quite dramatically with increasing temperature. The molar ellipticity of PRN60 at 90° C. was 28.8% less than the value at 25° C. The ability to reduce the intensity at 198 nm indicates that PRN60 contains significant structure in solution. The lack of two separate negative bands at 220 and 208 nm and the absence of the large positive band at 192 nm rules out any α-helical character for this peptide in solution. The CD spectrum of PRN60 (FIG. 4) also lacks the negative band near 216 nm and the large positive band between 195 and 200 nm which are characteristic of the spectra for a β-sheet structure (Woody, 1985, Circular Dichroism of Peptides. In: *The Peptides: Analysis, Synthesis, Biology*, 7:16–104 Academic Press, Inc. Orlando, Fla.; Johnson, 1988, Ann. Rev. Biophys. Chem. 17:145–166)

A previous model peptide study concluded that a CD spectrum similar to that observed here for PRN60 was characteristic of a random-coil peptide (Brahms and Brahms, 1980, J. Mol. Biol. 138: 149–178). This interpretation can now be reconsidered if one considers the model peptide used for this study was poly (PKLKL)n. This peptide motif, originally intended to be non-helical and non-beta sheet, is most compatible with the motif for a proline-rich poly-reverse turn protein. In fact, a turn is predicted to occur every (LPKL) with $pt=0.9\times10^{-4}$ when the Chou-Fasman criteria are applied to this sequence. Thus, this peptide sequence may actually be a standard for a poly-reverse turn protein and not a random-coil conformation.

Other proteins have been shown to possess a large negative peak at 198 nm (e.g., Ausio, et al., 1987, Biochemistry 26: 975–982; Johnson, 1988, Ann. Rev. Biophys. Chem 17: 145–166; Tatham, et al., 1985, Biochem. J. 226: 557–562; Madison and Schellman, 1990, Biopolymers 9: 65–94; Urry, 1987, J. Prot. Chem. 7: 1–34). An alternative interpretation for the CD spectrum of PRN60 is that this is the characteristic CD spectra of proline-rich poly β-turn structures. This CD spectrum is identical to that observed with the model compound N-acetyl-L-proline-N,N-diethylamide (AcProDMA) in which the CD spectrum is dominated by a large negative Cotton effect at 198 nm and is attributed to three π-π* transitions and a large n-π* transition in the tertiary amide (Madison & Schellman, 1970, Biopolymers 9: 511–567, 569–588). The large negative Cotton effect at 198 nm in $H_2O$ was shown to be characteristic of AcProDMA in the trans conformation. In contrast, the CD spectrum of AcProDMA in the cis conformation yields a large positive Cotton effect at 198 nm. The recorded spectrum could be represented as linear combination of the spectrum of the trans and cis isomers (Madison & Schellman, 1970, Biopolymers 9: 511–567, 569–588). The decrease in intensity at 198 nm observed with PRN60 at increasing temperatures indicates either that more cis proline is being formed as the temperature increases or that the β-turn helix in which the proline residues would be preferentially in the trans conformation (Matsushima, et al., 1990, Proteins: Structure, Function and Genetics 7: 125–155).

6.2.7. The PRN Domain of FeLV gp70

The present invention discloses a peptide corresponding to the proline-rich neutralization domain from the surface unit of gp70 of the feline leukemia virus forms a polyproline β-turn helix. A proline-rich domain is documented for retroviruses such as the murine leukemia virus (Ott, et al., 1990, J. Virol. 64: 757–766; Battini, et al., 1992, J. Virol. 66: 1468–1475) and the Gibbon ape leukemia virus (GaLV) (Delassus, et al., 1989, Virology 53: 205–213). The amphotrophic murine leukemia virus (MuLv) 4070A contains a proline-rich region (PR) that is composed of 33% proline, 18% serine, 11% threonine, 8% valine and 7% glycine. A similar domain is located in the external glycoprotein of Gibbon ape leukemia virus (GaLV) (Delassus, et al., 1989, Virology 53: 205–213) and contains 27% proline, 15% threonine, 10% leucine, 9% alanine and 9% serine. The retroviral proline-rich domains resemble in sequence composition and predicted repetitive structure, without the same sequence repeats, the human breast and pancreatic mucin (Gendler, et al., 1988, J. Biol. Chem. 26: 12820–12823; Lan, et al., 1990, Cancer Res. 50: 2997–3001). These sequences appear to represent retroviral versions of mucin type glycoproteins (Jentoft, 1990, Trends Biochem. Sci. 15: 291–294; Strouss and Dekker, 1992, Critical Reviews in Biochemistry and Molecular Biology 27(1/2): 57–92).

Examples of other proline-rich peptide fragments that have been studied include human breast and pancreatic epithelial duct mucin (Tendler, 1990, Biochem. J. 267: 733–737), Type IV and Type I collagen (Mayo, et al., 1991, Biochemistry 30: 8251–8267; Otter, et al., 1989, Biochemistry 28: 8003–8010), LC1 alkali light chain of skeletal myosin (Bhandari, et al., 1986, Eur. J. Biochem. 160: 349–356), the Spisula solidissima nuclear sperm-specific protein (Ausio, et el., 1987, Biochemistry 26: 975–982), and bovine elastin (Chang, et al., 1989, J. Biomol. Struct. and Dynam. 36: 122–127; Bhandary, et al., 1990, Int. J. Peptide Protein Res. 36: 122–127). In particular, the solution structure of peptide fragments of larger proteins which are immunogenic as fragments are of interest in examining the relationship between peptide structure in solution and induction of functional antibodies (Dyson, et al., 1988, J. Mol. Biol. 210: 201–217; Richman and Reese, 1988, Proc. Natl. Acad. Sci. USA 85: 1662–1666; Kotake, et al., 1990, Cell. Immunol. 126: 331–342; Dyson, et al., 1992, Biochemistry 31: 1458–1463). The sequence of PRN60 is incompatible with either α-helical or β-sheet secondary structure and is determined by our modeling to form ten reverse turns. Matsushima, et al. (1990, Proteins: Structure, Function and Genetics 7:125–155) has proposed that certain proline-rich repeat sequences form a secondary structure similar to poly-type I or III reverse turn motif called a polyproline β-turn helix Previous $^1$H-NMR studies with peptides of collagen (Mayo, et al., 1991, Biochemistry 30: 8251–8267; Otter, et al., 1989, Biochemistry 28: 8003–8010 and mucin (Tendler, 1990, Biochem. J. 267: 733–737) indicate that a multiple-turn motif might be stable in a peptide corresponding to a larger protein. Our $^1$H-NMR results show that protons in PRN60 are protected from $D_2O$ exchange. In fact, exchange was remarkably resistant to time and temperature.

The PRN peptides self-assemble in solution and form a complex whose $^1$H-NMR spectrum is very much like native PRN60 in $D_2O$. This type of behavior was recently shown to occur with *E. coli* Trp repressor protein (Tasayco and Carey, 1992, Science 225: 594–597). The self-assembly of Trp repressor peptides generated proteolytically could be followed by observing the proton chemical shift dispersion of the native protein, individual peptide fragments and reconstituted mixture in the amide proton region of the $^1$H-NMR spectrum. Peptide fragments of a bovine pancreatic trypsin inhibitor (BPTI) folding intermediate [5–55] also display the ability to fold into a native-like structure as determined by the chemical shift dispersion in the amide proton region and circular dichroism (Staley and Kim, 1990, Nature 344: 685–688).

Therefore, the structure formed by PRN60 in solution represents the native conformation found in the virion for three reasons: (i) sequence composition and modeling studies of intact surface unit (FeLV gp70) indicates that this sequence is only compatible with a β-turn helix motif, (ii) antibodies generated to the peptide free in solution and conjugated to KLH recognize the virion very well in ELISA, and (iii) monoclonal antibodies generated to native gp70 also bind to the peptide.

Therefore, it is demonstrated by $^1$H-NMR that PRN60 forms an ordered structure in solution with large conformational mobility that is long lived, and that peptide fragments of this structure will self-assemble into a native like conformation. The circular dichroism results verify that the solution conformation is not α-helical or β-sheet, and that the structure assumed contains primarily proline in the trans conformation. Proline in the trans conformation is consistent with proline in reverse turns. The intrinsic viscosity results suggest a non-random coil structure that is rod shaped. Therefore, PRN60 forms a polyproline β-turn helix and that region of gp70 is a separate folding domain of the surface unit protein.

TABLE 1

Synthetic peptides corresponding to FeLV-gp70 proline-rich neutralization domain (SEQ ID NO:6). Start and stop sites for the fragment peptides were determined by the intervals of the predicted turns.
PREDICTED TURNS IN PROLINE RICH NEUTRALIZATION DOMAIN

| Amino Acid # | Sequence | [a]Bend Probability $\times 10^{-4}$ | [b]$P_t$ |
|---|---|---|---|
| 233–236 | PPQA | 0.66 | 1.17 |
| 238–241 | GPNL | 4.10 | 1.31 |
| 243–246 | LPDQ | 1.98 | 1.15 |
| 248–251 | PPSR | 3.26 | 1.38 |
| 255–258 | TGSK | 0.87 | 1.23 |
| 263–266 | RPQT | 0.62 | 1.11 |
| 270–273 | APRS | 1.90 | 1.15 |
| 275–278 | APTT | 0.93 | 1.04 |
| 280–283 | GPKR | 1.88 | 1.26 |
| 285–288 | GTGD | 1.69 | 1.39 |

[a]probability of a bend at residue i through i + 4
[b]average conformational potential of this sequence; $P_t > 1.00$ and $P_t > P_\alpha$ & $P_\beta$ for a turn to be predicted.

7. EXAMPLE: PRODUCTION OF ANTI-PRN60 PEPTIDE ANTIBODIES AND EXPERIMENTAL VACCINATIONS WITH PRN60

7.1. Materials and Materials

Various procedures known in the art may be used for the production of anti-PRN60 peptide antibodies that bind to and neutralize FeLV. Any of the antibodies generated for use in the invention include but are not limited to polyclonal, monoclonal, chimeric, single chain and Fab fragments.

For the production of polyclonal antibodies, a vertebrate host may be immunized with the peptide alone or a peptide joined to a carrier molecule to promote an immune response. The immunogen may then be mixed with an adjuvant and injected into the vertebrate host according to a predetermined schedule. The animal is then periodically bled and the titer tested by PLL-ELISA. In the present example, the PRN60 peptide was either linked to KLH or left unlinked and utilized to immunize rabbits, mice and cats. In the case of rabbits and cats the adjuvant was initially Freund's complete adjuvant and followed by Freund's incomplete adjuvant.

Peptides were reacted in a solid-phase PLL-ELISA, which has been optimized for use with peptide antigens (Ball, J. M., 1990, Ph.D thesis, Louisiana State University, Baton Rouge). Briefly, poly-L-lysine (Mr 45–50K) is adsorbed onto the plastic surface of the microtiter plate. A low background with adequate signal (high signal to noise ratio) is achieved when PLL is bound to the wells of Immulon I (Dynatech Laboratories; Chantilly, Va.) 96-well microtiter plates and is coupled to the antigen with 1% glutaraldehyde in PBS. The PLL treated microtiter plates

TABLE 2

PROLINE RICH NEUTRALIZATION DOMAIN PEPTIDES

| PRN60 | (SEQ ID NO: 1) | | | | |
|---|---|---|---|---|---|
| | TITPPQAMGP NLVLPDQKPP | SRQSQTGSKV | ATQRPQTNES | APRSVAPTTV | GPKRIGTGDR |
| PRN42 | (SEQ ID NO: 2) | | | | |
| | TPPQAMGP NLVLPDQKPP | SRQSQTGSKV | ATQRPQTNES | APRS | |
| PRN21 | (SEQ ID NO: 3) | | | | |
| | TPPQAMGP NLVLPDQKPP | SRQ | | | |
| PRN2242 | (SEQ ID NO: 4) | | | | |
| | | SQTGSKV ATQRPQTNES APRS | | | |
| PRN4358 | (SEQ ID NO: 5) | | | | |
| | | | | VAPTTV GPKRIGTGDR | |

The sequences are underneath the name of each respective peptide from the amino to carboxy terminal. Peptide fragment start and stop sites correspond to intervals between predicted turns.

TABLE 3

MOLECULAR DIMENSION OF PRN60 FROM INTRINSIC VISCOSITY

| Intrinsic Viscosity [η] ml/g | Simha shape factor v | A/B[b] | A/B[c] |
|---|---|---|---|
| 7.49 | 10.7 | 9.1 | 9.7 |

[a]Summary of the molecular dimensions determined from instrinsic viscosity measurements of PRN60.
[b]Axial ratio determined by intrinsic viscosity.
[c]Axial ratio determined by molecular graphics program sybyl.

were then used directly in the ELISA based assay described below. Whole virus (FeLV-Theilen) was adsorbed directly onto the plastic surface of the microtiter plate with 1% gluteraldehyde in PBS. The whole virus containing microtiter plate was then used directly in the ELISA based assay described below.

The primary antibodies were diluted serially at 1/100, 1/1,000 and 1/10,000 in 10% BLOTTO (Carnation dry milk) and 10% horse serum in 0.01M phosphate buffer (pH 7.4) with 0.5M NaCl and 0.2% Tween 20. Primary antibody incubations were at room temperature for 30 minutes. The secondary antibody was goat anti-cat immunoglobulin G-horseradish peroxidase (Jackson Immuno Research Laboratories, Inc., West Grove, Pa.) with o-phenylenediamine dihydrochloride as the substrate. The secondary antibody was diluted at 1/5,000 in 10% BLOTTO (Carnation dry milk) and 10% horse serum in 0.01M phosphate buffer (pH 7.4), with 0.5M NaCl and 0.2% Tween 20 and was incubated for 30 minutes at room temperature. The ELISA wash solution was 1M NaCl and 0.2% Tween 20.

Mice were immunized subcutaneously with four doses of unlinked PRN60 peptide (100 micrograms per dose) in incomplete Freund's adjuvant at 2 week intervals. Two weeks following the last immunization, the mice were sacrificed and blood and spleens were collected for assays of humoral and cellular immune responses, respectively, elicited by the PRN60 immunogen. Antibody responses were measured in standard PLL-ELISA assays using PRN60 as substrate. Cellular immune responses were assayed by measuring in vitro proliferative responses ($^3$H-thymidine incorporation) of spleen cells from immunized mice in response to different amount of PRN60 peptide.

7.2. Results

Table 4 represents bleeds taken one month (1 boost) after immunization for rabbits and six weeks (2 boosts) after immunization for cats. In each case KHL linked peptide induced higher titer antibodies that reacted well with PRN60 and whole FeLV-Theilen. Unconjugated peptides induced lower titer antibodies to PRN60 and to FeLV-Theilen.

The ratio of the whole virus titer divided by the PRN60 titer provides a measure of the polyclonal antibodies ability to react with native protein (Table 5). Cats generated lower titer antibodies to PRN60, yet these antibodies had a 16 times greater ability to bind FeLV-Theilen. For example, PRN60 conjugated to KLH induced in a cat a titer of 4000 to PRN60 and a titer of 1500 to the whole virus (Table 4). In contrast, PRN60 conjugated to KLH induced a rabbit titer of 2200 to PRN60 and 520 to the whole virus. This disparity in the ability to induce virus reactive antibodies reduces to a factor of seven when unlinked titers are considered. However, the pattern of cats inducing lower peptide titers and higher virus titers is maintained with unlinked antigen (Tables 4 and 5). The covalently conjugated peptide induced antibodies that reacted with higher titers to the individual peptide fragments of PRN60 (PRN21, PRN2242, PRN4358), and this pattern was observed in rabbits and cats. The C-terminus of PRN60 appears to dominate the antibody response, especially in cats. The C-terminal segment induced three times higher titer with conjugated peptide and ten times higher titer with unconjugated peptide in cats. This pattern is broken somewhat in rabbits immunized with conjugated peptide. In this case, the middle segment and C-terminal segment induced 5–7 times higher titers that the N-terminal segment. The pattern of antibody reactivity induced by unconjugated peptide as immunogen is similar in rabbits and cats, with the C-terminal segment dominating.

Table 6 summarizes the humoral and cellular immune responses elicited by PRN60 immunization of mice. All of the immunized mice produced relatively high levels of PRN60-specific antibody, with calculated titers of 2000–3000. In addition, all of the mice appeared to develop significant cellular immune responses, as evidenced by the proliferative responses (2–3 stimulation index) to 1 microgram of PRN60 per 10,000 cells. These mouse immunization studies demonstrate that unlinked PRN60 peptide is highly immunogenic, even in the absence of a strong adjuvant and with a relatively mild immunization regimen. The induction of proliferative T-cell responses indicates that the PRN60 is able to bind to MHC class II molecules and stimulate T-helper cells that support the production of high levels of antibody.

Therefore, the present invention discloses peptides comprising a secondary structure which mimics the native structure of an FeLV envelope protein. These peptides may be utilized as immunogens in a variety of fashions as indicated throughout this specification. Disclosed in this specification is the ability of large synthetic peptides to (1) retain a native configuration; (2) stimulate antibodies reactive with the whole virus; and (3) elicit a cellular response in experimental vaccinations, leading to the conclusion that such peptides are candidates for use as a prophylactic vaccine as well as an immune enhancer to an initial vaccine. The PRN60 is exemplified in this specification as one such candidate for use in these vaccine applications.

The present invention is not to be limited in scope by the embodiments disclosed in the examples which are intended as illustrations of a few aspects of the invention, and any embodiments which are functionally equivalent are within the scope of the invention. Indeed, various modifications of the invention in addition to those shown and described herein will become apparent to those skilled in the art and are intended to fall within the scope of the appended claims.

TABLE 4

| | | Titers[a] of Anti-PRN60 antibodies | | | | |
|---|---|---|---|---|---|---|
| Sp./ | Conj(?) | PRN60 | Whole[b] Virus | 21[c] | 2242[d] | 43580[e] |
| cat | yes | 4000 | 1500 | 420 | 420 | 1500 |
| | no | 1200 | 90 | 41 | 290 | 470 |
| rabbit | yes | 22000 | 520 | 330 | 2000 | 1500 |
| | no | 7500 | 80 | 28 | 380 | 2700 |

[a]titer is defined as the inverse of the dilution to yield an absorbance of 1.0 in a peptide ELISA
[b]FeLV theilen
[c]Amino acids 1 through 21 of PRN60 (PRN21)
[d]Amino acids 22 through 42 of PRN60 (PRN2242)
[e]Amino acids 43 through 58 of PRN60 (PRN4358)

TABLE 5

| | Antibody Reactivity to Native Protein | |
|---|---|---|
| Species | Conjugation | Ratios FeLV/PRN60[a] |
| cat | yes | .375 |
| | no | .075 |
| rabbit | yes | .024 |
| | no | .011 |

[a]Titer of anti-PRN60 to FeLV-Theilen divided by the titer to the immunizing antigen (PRN60).

TABLE 6

| Antibody and Cellular Immune Responses in Mice Immunized with PRN60 | | | |
|---|---|---|---|
| Mouse Index | ELISA Reactivity[a] | Antibody Titer[b] | Stimulation[c] |
| 1 | 1.3 | 2,500 | 2.0 |
| 2 | 1.1 | 2,500 | 2.3 |
| 3 | 1.0 | 3,000 | 3.0 |

[a]Absorbance in PLL-ELISA against PRN60 at a serum dilution of 1:500.
[b]Calculated end point titer against PRN60 in PLL-ELISA.
[c]T-cell proliferation of spleen cells (10,000) incubated with 1 mg/ml of PRN60. The stimulation index is calculated as the ratio of $^3$H-thymidine incorporation in cells incubated with peptide antigen compared to cells in the absence of antigen.

What is claimed is:

1. A peptide having the amino acid sequence of SEQ ID NO:1.
2. The peptide of claim 1 conjugated to a carrier protein.
3. The peptide of claim 2 wherein said carrier protein is keyhole limpet hemocyanin.
4. A peptide of from 50 to 60 amino acids in length and having at least 80% amino acid homology to the sequence of SEQ ID NO:1, wherein said peptide induces inducing the production of antibodies that bind to feline leukemia virus.
5. The peptide of claim 4 conjugated to a carrier protein.
6. The peptide of claim 5 wherein said carrier protein is keyhole limpet hemocyanin.
7. A peptide of from 50 to 60 amino acids in length and having at least 80% amino acid homology to the sequence of SEQ ID NO:1, wherein said peptide forms a polyproline beta turn helix in solution and induces inducing the production of antibodies that bind to feline leukemia virus.
8. The peptide of claim 7 conjugated to a carrier protein.
9. The peptide of claim 8 wherein said carrier protein is keyhole limpet hemocyanin.
10. A composition comprising the peptide of any one of claims 1–3 and an adjuvant.
11. A composition comprising the peptide of any one of claims 4–6 and an adjuvant.
12. A composition comprising the peptide of any one of claims 7–9 and an adjuvant.

* * * * *